United States Patent
Chung et al.

(10) Patent No.: US 10,238,710 B2
(45) Date of Patent: Mar. 26, 2019

(54) PEPTIDE HAVING ANTI-INFLAMMATORY, OSTEOGENIC AND HAIR GROWTH PROMOTING ACTIVITIES, AND USE OF SAME

(71) Applicant: CAREGEN CO., LTD., Anyang-si (KR)

(72) Inventors: Yong Ji Chung, Yongin-si (KR); Eun Mi Kim, Yongin-si (KR); Eung Ji Lee, Anyang-si (KR); Kyoung Mi Cho, Cheonan-si (KR); A Reum Han, Icheon-si (KR)

(73) Assignee: CAREGEN CO., LTD., Anyang-si (KR)

( * ) Notice: Subject to any disclaimer, the term of this patent is extended or adjusted under 35 U.S.C. 154(b) by 0 days.

(21) Appl. No.: 15/307,943

(22) PCT Filed: Nov. 21, 2014

(86) PCT No.: PCT/KR2014/011272
§ 371 (c)(1),
(2) Date: Oct. 31, 2016

(87) PCT Pub. No.: WO2015/174598
PCT Pub. Date: Nov. 19, 2015

(65) Prior Publication Data
US 2017/0049847 A1    Feb. 23, 2017

(30) Foreign Application Priority Data
May 13, 2014    (KR) .................. 10-2014-0057191

(51) Int. Cl.
| A61K 38/08 | (2006.01) |
| C07K 7/06 | (2006.01) |
| A61K 8/64 | (2006.01) |
| A61Q 7/00 | (2006.01) |

(52) U.S. Cl.
CPC .............. *A61K 38/08* (2013.01); *A61K 8/64* (2013.01); *A61Q 7/00* (2013.01); *C07K 7/06* (2013.01); *A61K 2800/74* (2013.01)

(58) Field of Classification Search
None
See application file for complete search history.

(56) References Cited

U.S. PATENT DOCUMENTS 4,816,449 A * 3/1989 Hahn .................. C07K 5/0819
                                             514/12.2
6,417,327 B1 * 7/2002 Oka ..................... C07K 14/50
                                               530/300

FOREIGN PATENT DOCUMENTS

| JP | H07-025783 A | 1/1995 |
| JP | 2007-537976 A | 12/2007 |
| JP | 2008-81483 A | 4/2008 |
| JP | 2010-535758 A | 11/2010 |
| JP | 2012-515769 A | 7/2012 |
| JP | 2013-28587 A | 2/2013 |
| WO | WO-2007/049905 A1 | 5/2007 |
| WO | WO-2013/137505 A1 | 9/2013 |

OTHER PUBLICATIONS

Tokuriki et al., 2009, Curr. Opin. Struc. Biol. 19:596-604.*
Bhattacharya et al. (2017, PLoS ONE 12(3): e0171355, https://doi.Org/10.1371/journal.pone.0171355).*
Baum et al. (2016, Clinic. Rev. Allerg. Immunol. 51:1-15).*
Chai et al., "Inverse agonist activity of agouti and agouti-related protein," Peptides. 24(4):603-9 (2003).
Mundy et al., "Investigation of the role of the agouti signaling protein gene (ASIP) in coat color evolution in primates," Mamm Genome. 17(12):1205-13 (2006).
Office Action dated Oct. 3, 2017 for Japanese Patent Application No. 2016-565493, Tanaka et al., "Peptide having anti-inflammatory, osteogenic and hair growth promoting activities, and use of same," filed Nov. 21, 2014 (11 pages).
Rieder et al., "Mutations in the agouti (ASIP), the extension (MC1R), and the brown (TYRP1) loci and their association to coat color phenotypes in horses (*Equus caballus*)," Mamm Genome. 12(6):450-5 (2001).

(Continued)

*Primary Examiner* — Elizabeth C. Kemmerer
(74) *Attorney, Agent, or Firm* — Clark & Elbing LLP; Susan M. Michaud

(57) ABSTRACT

Provided is a peptide, which has an anti-inflammatory activity and an activity for promoting osteogenic differentiation, formed from the amino acid sequence selected from the group comprising the amino acid sequences of SEQ ID NO: 1, SEQ ID NO: 2, and SEQ ID NO: 3. And provided is a peptide, which has a hair growth promoting activity, formed from the amino acid sequence selected from the group comprising the amino acid sequences of SEQ ID NO: 1 and SEQ ID NO: 2. A peptide formed from the amino acid sequence of SEQ ID NO: 1, SEQ ID NO: 2, or SEQ ID NO: 3, according to the present invention, consequently shows an anti-inflammatory activity by inhibiting an inflammatory cytokine expression and proliferation of inflammatory cells, and consequently promotes osteogenic differentiation by increasing phosphorylation of PI3K, Smad1, Smad5 and Smad8, which contribute to osteogenesis, and by increasing ALP, OPG and BSP expressions. And a peptide formed from the amino acid sequence of SEQ ID NO: 1 or SEQ ID NO: 2, according to the present invention, consequently shows efficacy for preventing hair loss and promoting hair growth by promoting proliferation of hair follicle cells and human umbilical vein endothelial cells, increasing phosphorylation of EPK, increasing expressions of PI3K, β-catenin, IGF-1, KGF and Wnt3a which are proteins that contribute to hair growth, and reducing an expression of DKK-1 which is a hairless gene.

21 Claims, 42 Drawing Sheets

Specification includes a Sequence Listing.

(56) References Cited

OTHER PUBLICATIONS

Anonymous, "Caregen 2012—Biomimetic Peptide/Growth Factor," retrieved from: <https://d1gm0mynlzh1bh.cloudfront.net/docs/caregen-catalogue.pdf> on Nov. 27, 2017, (Apr. 26, 2012) (64 pages).

Cheng et al., "The TNF receptor superfamily: role in immune inflammation and bone formation," Immunologic Research. 27(2-3):287-94 (2003).

Partial Supplementary European Search Report dated Dec. 14, 2017 for European Patent Application No. 14892017.6, Chung et al., "Peptide Having Anti-Inflammatory, Osteogenic and Hair Growth Promoting Activities, and Use of Same," filed Nov. 21, 2014 (11 pages).

Extended European Search Report dated Jul. 9, 2018 for European Patent Application No. 18161612.9, Chung et al., "Peptide Having Anti-Inflammatory, Osteogenic and Hair Growth Promoting Activities, and Use of Same," filed Nov. 21, 2014 (5 pages).

Kamato et al., "Transforming growth factor—[beta] signalling: Role and consequences of Smad linker region phosphorylation," Cell Signal. 25(10):2017-24 (2013).

Lee et al., "Synthetic peptides containing ITIM-like sequences of IREM-1(CD300F) differentially regulate MyD88 and TRIF-mediated TLR signalling through activation of SHP and/or PI3K," Clin Exp Immunol. 167(3):438-46 (2012).

\* cited by examiner

PEPTIDE HAVING ANTI-INFLAMMATORY, OSTEOGENIC AND HAIR GROWTH PROMOTING ACTIVITIES, AND USE OF SAME

TECHNICAL FIELD

The present patent application claims priority to and the benefit of Korean Patent Application No. 10-2014-0057191 filed in the Korean Intellectual Property Office on 13 May 2014, the entire contents of which are incorporated herein by reference.

The present invention relates to a peptide having anti-inflammatory, osteogenic, and hair growth promoting activities, and to a use thereof.

BACKGROUND ART

Tumor necrosis factor-α (TNF-α) is produced by macrophages activated in a host immune response for bacterial infection and tumor diseases, and various several cells. This cytokine has been known as an important medium in the inflammatory response, and is an inflammatory cytokine that plays a key role in inflammatory diseases, such as rheumatoid arthritis (RA), psoriatic arthritis, Crohn's disease, psoriasis, and ankylosing spondylitis (AS). For example, TNF-α keeps synovial inflammation and continuously destroys bones and cartilages in rheumatic arthritis. Therefore, the inhibition of the specific biological activity of TNF-α is required, and thus various biological preparations for inhibiting TNF-α have been developed for the purpose of preventing the cellular response mediated by TNF-α and adjusting activities of proinflammatory cytokines and the procedures regulated by TNF-α.

Meanwhile, the bone is one of the important parts of the human body that structurally support muscles or organs and store calcium or other essential minerals, in other words, materials, such as phosphorus and magnesium in the body. Therefore, adult bones after the completion of growth maintain balance thereof until death without stopping while the generation and absorption procedures of removing old bones and substituting for new bones are repeated very dynamically and continuously.

It has been known that two kinds of cells are greatly involved in bone remodeling. One of the two kinds of cells corresponds to osteoblasts, which generate bones, and the other corresponds to osteoclasts, which destroy bones. The osteoblasts generate a receptor activator of nuclear factor-KB ligand (RANKL) and a decoy receptor thereof, that is, osteoprotegerin (OPG). When RANKL binds to RANK, which is a receptor on a surface of osteoclast progenitor cells, the osteoclast progenitor cells mature into osteoclasts, resulting in bone resorption. However, the binding of OPG to RANKL cuts off the binding between RANKL and RANK, thereby suppressing the formation of osteoclasts, thus preventing unnecessary bone resorption (Theill L E. et al., Annu Rev Immunol., 20:795-823 (2002); Wagner E F. et al., Curr Opin Genet Dev., 11:527-532 (2001)). The resorption or destruction of old bones is made by osteoclasts generated in blood cells (hematopoietic stem cells), and the osteoclasts make holes in bones to release a small amount of calcium into the blood, and the calcium is used to maintain the body functions (William J. et al., Nature., 423:337342 (2003)). Meanwhile, osteoblasts generated from bone cells fill the holes with collagen and cover the holes with hydroxyapatite of calcium and phosphorus, thereby making new rigid bones to reconstruct skeletons (Stains J P. et al., Birth Defects Res C Embryo Today., 75(1):72-80 (2005)). It takes about 100 days to disrupt old bones and rebuild new bones (Schwarz E M. et al., Curr Opin Orthop., 11:329-335 (2000)). While 100% of calcium content in bone is changed within 1 year in an infant, about 10-30% of the skeleton is rebuilt by the bone remodeling in an adult every year. Only if the bone destroying rate and the bone forming rate are equal, the bone density can be maintained as before. The imbalance in important bones may cause many diseases, and particularly, the diseases associated with bone damage due to osteoporosis and bone metastasis of cancer cells are representative.

Osteoporosis is a disorder in which bone mass decreases by various causes and the risk of bone fracture continuously increases due to the degeneration of microstructure in bone tissue. Osteoporosis is a condition in which the contents of minerals (e.g., calcium) and substrates of bone have been reduced, and osteoporosis occurs when the bone destroying action becomes superior to the bone forming action due to the imbalance of bone remodeling (Iqbal M M., South Med J., 93(1):2-18 (2000)). While the inner structure of normal bones has a compact structure, such as a mesh, the osteoporosis bone shows a widened space between structures and a thinner micro-architecture that becomes susceptible to skeletal fractures by even the slight impact. Osteoporosis diseases are classified into postmenopausal osteoporosis, in which the bone loss (2-3% a year) promptly appears upon initiation of menopause and the risk of spine compression and wrist bone fracture is increased; senile osteoporosis, in which it is developed slowly (0.5-1% a year) in elder men and women aged more than 70 years and induces gradual bone loss of hip and spine bones; and secondary osteoporosis, which is developed by diseases (endocrine diseases, gastrointestinal diseases, and malignant tumors), drugs (adrenal cortical hormones, anticancer chemotherapy, thyroid hormones, anticonvulsants, antiplatelets, methotexate, cyclosporine and GnRH), alcohol, smoking or accident, regardless of age (Rosen C J., N Engl J Med., 353(6):595-603 (2005); Davidson M., Clinicain Reviews., 12(4):75-82 (2002)).

Breast cancer, prostate cancer, or multiple myeloma are usually accompanied with bone metastasis (Kozlow W. et al., J Mammary Gland Biol Neoplasia., 10(2):169-180 (2005)), and the lifespan of patients having such cancers has been known to be dependent on bone metastasis. The reason why the mortality of patients having breast or prostate cancer is increased is that cancer cells are selectively metastasized into bones. The bone metastasis observed in breast cancer is almost an osteolytic metastasis leading to bone destruction, and the osteolytic metastasis has been known to be caused by the stimulation of osteoclasts rather than the direct influence of breast cancer cells on bones (Boyde A. et al., Scan Electron Microsc., 4:1537-1554 (1986)). Whereas, the bone metastasis found in prostate cancer is an osteoblastic metastasis. The osteoblastic metastasis has also been known to be closely associated with osteolysis. The cancer cells entering bones proliferate in bone-surrounding microenvironments to stimulate the activity of osteoclasts or osteoblasts, thereby determining whether the subsequent bone metastasis is osteolytic or osteoblastic (Choong P F. et al., Clin Orthop Relat Res., 415S:S19-S31 (2003)). The bone metastasis of cancer cells occurs in about 80% of breast cancer patients, and the metastasized breast cancer cells activate osteoclasts (Bendre M., et al., Clin Orthop Relat Res., 415(Suppl):S39-S45 (2003); Palmqvist P. et al., J Immunol., 169(6):3353-3362 (2002)). The activated osteoclasts destroy the balance of the bone-surrounding microenvironments to cause osteolysis, resulting in frequent pathological fractures, and also causing bone-related diseases, such as leukoerythroblastic anaemia, bone deformity, hypercalcemia, pain, and nervecompression syndromes (Roodman G D., N Engl J Med., 350:1655-1664 (2004)).

According to the health insurance medical expense payment materials analyzed by Health Insurance Policy Institute of Korean National Health Insurance Corporation from 2001 to 2008, the number of patients of "hair loss diseases" is estimated at 103,000 people in 2001, at 142,000 people in 2005 and at 165,000 people in 2008. It has increased by 60% in recently seven years. The number of patients in their 20 s to 40 s is estimated at 114,000 people and it is accounted for 69.5% of whole patients. In addition, the number of patients in their 10 s is estimated at more than 22,000 people. The number of male patients is estimated at 84,000, and at 80,000 female patients, which is slightly more than that of male. The number of patients of "hair loss" disease in 2008 Korean Health Insurance treatment are alopecia areata (130,000 people), cicatricial alopecia (20,000 people), androgenetic alopecia (9,000 people) and other nonscarring hair loss (8,000 people) in order.

Abroad, according to data in June 2003 International Hair and Beauty Studies, there are 250 million hair loss patients, and the prevalence rate of hair loss patients between the ages of twenty-four and fifty years old is 30-65%. In China, the number of hair loss patients is 300 million people in 2008. 30% of males in their 30 s and 50% of males in their 50 s show signs of hair loss, and the number of hair loss patients increases by 10-15% every year. In Japan, prevalence rate of hair loss is 26.5%, and the number of hair loss patients is estimated at 12.93 million people.

Currently, the preparations for treating hair loss are largely classified into pharmaceutical medicines, quasi-drugs, and cosmetics. The accessible prescription drug given by doctors is "Propecia", which was developed and marketed by Merck (U.S.), and its active ingredient Finasteride has been approved as a drug for treating hair loss from the U.S. FDA in December 1997. Finasteride inhibits 5-α-reductase which converts testosterone to dihydrotestosterone (DHT), whereby it results in growth of thick and long hair. Although it has an effect for alleviating hair loss in the short term, side effects such as impotence, sexual dysfunction, and male breast enlargement have been reported. Minoxidil has been recognized in safety and efficacy as a drug available to purchase without a doctor's prescription, and it has been firstly approved as a spread drug for treating hair loss from the U.S. FDA in December 1997. It improves blood circulation and opens potassium channels to promote hair growth, but it has local responses, such as itching, rash, and frequent pulse.

Quasi-products for hair loss prevention and hair growth functions approved from Korea Food & Drug Administration include "Mobalryeok confidence" (CJ lion), "Hair Tonic" (Moracle), and "Moaenmoah" (LG Household & Health Care). As cosmetics, shampoos or products used in the scalp and hair have been sold to maintain or promote the health of skin and hair. The human hair cycle is largely divided into growth (anagen), cessation (catagen), and rest (telogen) stages. In the anagen stage, the activity of hair papillae is active, leading to active cell division, and thus the hair grows rapidly. The lifespan of hairs in the anagen stage ranges from 3 to 6 years, depending on the kind of hair. The hairs in the anagen stage accounts for 80-90% of the entire hair. When hair loss is in progress, shorter anagen and longer catagen lead to the reduction of the proportion of the hair in the anagen stage in the entire hair. In the catagen stage after the anagen stage, the generation of hairs becomes slower, and thus, the cell division and growth are ultimately stopped. The catagen stage continues for 1-1.5 months and occupies 1% of total hairs. In the telogen stage, which is the last stage of growth, hair follicles, and hair papillae are completely separated from each other, and the hair follicles are gradually contracted, and the hair roots are pushed upward, and finally the hair falls out. This stage lasts for about 3-4 month, and accounts for 4-14% of total hairs. When the activity of the hair papillae is again active after the telogen stage is ended, the hair papillae for new hair are generated, and the hair at the telogen stage is pushed upward, and completely removed from the scalp.

Throughout the entire specification, many papers and patent documents are referenced and their citations are represented. The disclosure of the cited papers and patent documents are entirely incorporated by reference into the present specification, and the level of the technical field within which the present invention falls, and the details of the present invention are explained more clearly.

DETAILED DESCRIPTION OF THE INVENTION

Technical Problem

The present inventors have endeavored to develop excellent peptides having a biologically effective activity, and as a result, the present inventors have established that a peptide composed of one amino acid sequence selected from the group consisting of amino acid sequences of SEQ ID NO: 1, SEQ ID NO: 2, and SEQ ID NO: 3 exhibits anti-inflammatory and osteogenic activities, and a peptide composed of one amino acid sequence selected from the group consisting of amino acid sequences of SEQ ID NO: 1 and SEQ ID NO: 3 has a hair growth promoting activity, and then have completed the present invention.

Accordingly, an aspect of the present invention is to provide a peptide having an anti-inflammatory activity.

Another aspect of the present invention is to provide a peptide having an osteogenic differentiation promoting activity.

Another aspect of the present invention is to provide a peptide having a hair growth promoting activity.

Another aspect of the present invention is to provide an anti-inflammatory composition.

Another aspect of the present invention is to provide a composition for promoting osteogenic differentiation.

Another aspect of the present invention is to provide a composition for preventing hair loss and promoting hair growth.

Other purposes and advantages of the present disclosure will become more obvious with the following detailed description of the invention, claims, and drawings.

Technical Solution

In accordance with an aspect of the present invention, there is provided a peptide having an anti-inflammatory activity, composed of one amino acid sequence selected from the group consisting of amino acid sequences of SEQ ID NO: 1, SEQ ID NO: 2, and SEQ ID NO: 3.

In accordance with another aspect of the present invention, there is provided a peptide having an osteogenic differentiation promoting activity, composed of one amino acid sequence selected from the group consisting of amino acid sequences of SEQ ID NO: 1, SEQ ID NO: 2, and SEQ ID NO: 3.

In accordance with another aspect of the present invention, there is provided a peptide having a hair growth promoting activity, composed of one amino acid sequence selected from the group consisting of amino acid sequences of SEQ ID NO: 1 and SEQ ID NO: 3.

The present inventors have endeavored to develop excellent peptides having a biologically effective activity, and as a result, the present inventors have established that a peptide composed of one amino acid sequence selected from the group consisting of amino acid sequences of SEQ ID NO: 1, SEQ ID NO: 2, and SEQ ID NO: 3 exhibits anti-inflammatory and osteogenic activities, and a peptide composed of one amino acid sequence selected from the group consisting of amino acid sequences of SEQ ID NO: 1 and SEQ ID NO: 3 has a hair growth promoting activity.

The peptide of the present invention includes an amino acid sequence of SEQ ID NO: 1, SEQ ID NO: 2, or SEQ ID NO: 3. Specifically, the peptide of the present invention is essentially composed of an amino acid sequence of SEQ ID NO: 1, SEQ ID NO: 2, or SEQ ID NO: 3.

According to an embodiment, the peptide composed of an amino acid sequence of SEQ ID NO: 1, SEQ ID NO: 2, or SEQ ID NO: 3, of the present invention inhibits the expression of an inflammatory cytokine and suppresses the proliferation of inflammatory cells, resultantly exhibiting an anti-inflammatory activity.

According to another embodiment of the present invention, the peptide composed of an amino acid sequence of SEQ ID NO: 1, SEQ ID NO: 2, or SEQ ID NO: 3 of the present invention increases the phosphorylation of PI3K, Smad1, Smad5, and Smad8, which are involved in osteogenesis, and increases the expression of ALP, OPG, and BSP, resultantly promoting osteogenic differentiation.

According to another embodiment of the present invention, the peptide composed of SEQ ID NO: 1 or SEQ ID NO: 3 of the present invention promotes the proliferation of hair follicle cells and umbilical vein endothelial cells, increases the phosphorylation of ERK, increases the expression of PI3K, β-catenin, IGF-1, KGF, and Wnt3a, which are proteins involved in hair growth, and reduces the expression of the hair loss gene DKK-1, resultantly exhibiting hair loss preventing and hair growth promoting activities.

As used herein, the term "peptide" refers to a linear molecule in which amino acid residues bind to each other via a peptide linkage. The peptides of the present invention may be prepared by a chemical synthesis method known in the art, especially, solid-phase synthetic techniques (Merrifield, J. Amer. Chem. Soc. 85:2149-54 (1963); Stewart, et al., Solid Phase Peptide Synthesis, 2nd. ed., Pierce Chem. Co.: Rockford, 111 (1984)) or liquid-phase synthetic techniques (U.S. Pat. No. 5,516,891).

According to an embodiment of the present invention, a protective group, which is selected from the group consisting of an acetyl group, a fluorenyl methoxy carbonyl group, a formyl group, a palmitoyl group, a myristyl group, a stearyl group, and polyethylene glycol (PEG), may be linked to the N- or C-terminal of the peptide.

The foregoing amino acid modification significantly improves the stability of the peptide of the present invention. As used herein, the term "stability" refers to storage stability (e.g., room-temperature storage stability) as well as "in vivo" stability. The foregoing protective group protects the peptides of the present invention from the attack of in vivo protein cleavage enzymes.

According to another aspect of the present invention, the present invention provides an anti-inflammatory composition containing, as an active ingredient, the foregoing peptide composed of one amino acid sequence selected from the group consisting of amino acid sequences of SEQ ID NO: 1, SEQ ID NO: 2, and SEQ ID NO: 3.

Since the composition of the present invention contains, as an active ingredient, the foregoing peptide composed of an amino acid sequence of SEQ ID NO: 1, SEQ ID NO: 2, or SEQ ID NO: 3, the overlapping contents between the composition and the peptide will be omitted to avoid excessive complication of the present specification.

As validated in the following examples, the peptide composed of an amino acid sequence of SEQ ID NO: 1, SEQ ID NO: 2, or SEQ ID NO: 3 of the present invention is very effective in the prevention or treatment of anti-inflammatory diseases by inhibiting the expression of an inflammatory cytokine, suppressing the proliferation of inflammatory cells, and suppressing the inflammatory response.

The inflammatory diseases to which the anti-inflammatory composition of the present invention may be applied include, but are not limited to: acute or chronic inflammatory diseases, such as inflammatory skin diseases (e.g., asthma, eczema, psoriasis, allergies, rheumatoid arthritis, psoriatic arthritis, atopic dermatitis, acne, atopic rhinitis (hay fever), allergic dermatitis (eczema), chronic sinusitis, or seborrheic dermatitis), bone diseases, gastritis, gout, gouty arthritis, ulcers, chronic bronchitis, acute lung injury, lung inflammation, airway hypersensitivity, inflammatory bowel disease (e.g., Crohn's disease, ulcerative colitis), ankylosing spondylitis, sepsis, septic shock, vasculitis, and bursitis; autoimmune diseases, such as lupus, polymyalgia rheumatic, scleroderma, Wegener's granulomatosis, temporal arteritis, cryoglobulinemia, and multiple sclerosis; transplant rejection; cancers including solid tumors (e.g., lung, CNS, intestine, kidney, and pancreas); Alzheimer's disease; atherosclerosis; viral infections (e.g., HIV or influenza); chronic viral infections (e.g., Epstein-Barr virus, cytomegalovirus, herpes simplex virus); or ataxia telangiectasia.

According to an embodiment of the present invention, the anti-inflammatory composition of the present invention may be prepared as a pharmaceutical composition or a cosmetic composition.

The composition of the present invention may be used as a pharmaceutical composition containing: (a) a pharmaceutically effective amount of the foregoing peptide of the present invention; and (b) a pharmaceutically acceptable salt.

As used herein, the term "pharmaceutically effective amount" refers to an amount sufficient to attain efficacy or activity of the foregoing peptide.

The pharmaceutically acceptable carrier contained in the pharmaceutical composition of the present invention is conventionally used for the formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil. The pharmaceutical composition of the present invention may further contain a lubricant, a wetting agent, a sweetening agent, a flavoring agent, an emulsifier, a suspending agent, a preservative, and the like, in addition to the above ingredients. Suitable pharmaceutically acceptable carriers and preparations are described in detail in *Remington's Pharmaceutical Sciences* (19th ed., 1995).

The pharmaceutical composition of the present invention may be administered orally or parenterally, and examples of the parenteral administration may include intravenous, subcutaneous, intramuscular, intraperitoneal, local, and transdermal injections.

The appropriate dose of the pharmaceutical composition of the present invention varies depending on factors, such as the formulating method, manner of administration, patient's age, body weight, gender, morbidity, and food, time of administration, route of administration, excretion rate, and response sensitivity. An ordinarily skilled practitioner can easily determine and prescribe the dose that is effective for the desired treatment or prevention. According to a preferable embodiment of the present invention, the daily dose of the pharmaceutical composition of the present invention is 0.0001-200 μg.

In addition, the pharmaceutical composition of the present invention is formulated in a unit dosage form or into a multidose container, using a pharmaceutically acceptable carrier and/or excipient according to the method that is easily conducted by a person having an ordinary skill in the art to which the present invention pertains. Here, the dosage form may be a solution in an oily or aqueous medium, a suspension, an emulsion, an extract, a powder, granules, a tablet, a capsule, or a gel (e.g., a hydrogel), and may further include a dispersant or a stabilizer.

The composition of the present invention may be used as a cosmetic composition containing: (a) a cosmetically effective amount of the foregoing peptide; and (b) a cosmetically acceptable carrier.

As used herein, the term "cosmetically effective amount" refers to an amount that is sufficient to attain the efficacy of the composition of the present invention described above.

The cosmetic composition of the present invention may be formulated into any dosage form that is conventionally prepared, and examples thereof may include a solution, a suspension, an emulsion, a paste, a gel, a cream, a lotion, a powder, a soap, a surfactant-containing cleansing, an oil, a powder foundation, an emulsion foundation, a wax foundation, and a spray, but are not limited thereto. More specifically, the cosmetic composition of the present invention may be prepared in a dosage form of an emollient lotion, nutritional emulsion, nutritional cream, message cream, essence, eye cream, cleansing cream, cleansing foam, cleansing water, facial pack, spray or powder.

In cases where the dosage form of the present invention is a paste, a cream, or a gel, the carrier component thereof may include animal fibers, vegetable fibers, wax, paraffin, starch, tragacanth, cellulose derivatives, polyethylene glycol, silicone, bentonite, silica, talc, or zinc oxide.

In cases where the dosage of the present invention is a powder or a spray, the carrier component thereof may include lactose, talc, silica, aluminum hydroxide, calcium silicate, or a polyamide powder. In cases where the dosage form of the present invention is especially a spray, the dosage form may additionally include a propellant, such as, chlorofluorohydrocarbon, propane/butane, or dimethyl ether.

In cases where the dosage form of the present invention is a solution or an emulsion, the carrier component thereof may include a solvent, a solubilizer, or an emulsifier, for example water, ethanol, isopropanol, ethyl carbonate, ethyl acetate, benzyl alcohol, benzyl benzoate, propylene glycol, 1,3-butyl glycol oil, glycerol fatty esters, polyethylene glycol, or fatty acid esters of sorbitan.

In cases where the dosage form of the present invention is a suspension, the carrier component thereof may include liquid diluents, such as water, ethanol, and propylene glycol; suspending agents, such as, ethoxylated isostearyl alcohol, polyoxyethylene sorbitol ester, and polyoxyethylene sorbitan ester; microcrystalline cellulose; aluminum metal hydroxide; bentonite; agar; or tragacanth.

In cases where the dosage form of the present invention is a surfactant-containing cleansing, the carrier component thereof may include aliphatic alcohol sulfate, aliphatic alcohol ether sulfate, sulfosuccinate monoester, isothinate, imidazolium derivatives, methyl taurate, sarcosinate, fatty acid amide ether sulfate, alkyl amido betaine, aliphatic alcohol, fatty acid glyceride, fatty acid diethanolamide, vegetable oil, lanoline derivatives, or ethoxylated glycerol fatty acid ester.

The components contained in the cosmetic composition of the present invention include compositions that are commonly used in the cosmetic composition, in addition to the peptides, as active ingredients, and the carrier component thereof, and for example, may include common aids, such as an antioxidant, a stabilizer, a solubilizer, vitamins, a pigment, and a flavor.

According to another aspect of the present invention, the present invention provides a composition for promoting osteogenic differentiation, containing, as an active ingredient, the foregoing peptide composed of one amino acid sequence selected from the group consisting of amino acid sequences of SEQ ID NO: 1, SEQ ID NO: 2, and SEQ ID NO: 3.

Since the composition of the present invention contains, as an active ingredient, the foregoing peptide composed of an amino acid sequence of SEQ ID NO: 1, SEQ ID NO: 2, or SEQ ID NO: 3, the overlapping contents between the composition and the peptide will be omitted to avoid excessive complication of the present specification.

As validated in the following examples, the composition containing, as an active ingredient, the peptide composed of an amino acid sequence of SEQ ID NO: 1, SEQ ID NO: 2, or SEQ ID NO: 3 of the present invention promotes the differentiation of osteoblast lines. Therefore, the composition of the present invention can effectively promote the osteogenic differentiation.

According to an embodiment of the present invention, the composition of the present invention increases the phosphorylation of PI3K, Smad1, Smad5, and Smad8, which are involved in osteogenic differentiation, and increases the expression of OPG, ALP, and BSP genes, which are osteogenic differentiation markers.

According to another embodiment of the present invention, the composition of the present invention can be used in the alleviation or treatment of bone diseases.

According to an embodiment of the present invention, the bone diseases, which can be alleviated or treated by the composition of the present invention, include osteoporosis, childhood osteoporosis, osteogenesis imperfecta, osteomalacia, bone necrosis, rickets, osteomyelitis, alveolar bone loss, Paget's disease of bone, hypercalcemia, primary hyperparathyroidism, metastatic bone diseases, myeloma, bone loss in rheumatoid arthritis, bone loss resulting from cancers, fibrous dysplasia, aplastic bone disease, metabolic bone diseases, or bone mass loss with age, but are not limited thereto.

The composition for promoting osteogenic differentiation of the present invention may be prepared as a pharmaceutical composition.

According to another aspect of the present invention, the present invention provides a composition for preventing hair loss or promoting hair growth, the composition containing, as an active ingredient, the foregoing peptide composed of one amino acid sequence selected from the group consisting of amino acid sequences of SEQ ID NO: 1 and SEQ ID NO: 3.

Since the composition of the present invention contains, as an active ingredient, the foregoing peptide composed of an amino acid sequence of SEQ ID NO: 1 or SEQ ID NO: 3, the overlapping contents between the composition and the peptide will be omitted to avoid excessive complication of the present specification.

As validated in the following examples, the composition containing, as an active ingredient, the peptide composed of SEQ ID NO: 1 or SEQ ID NO: 3 of the present invention promotes the proliferation of hair follicle cells or umbilical vein endothelial cells, increases the phosphorylation of ERK, increases the expression of PI3K, β-catenin, IGF-1, KGF, and Wnt3a, which are proteins involved in hair growth, and reduces the expression of the hair loss gene DKK-1, resultantly exhibiting hair loss preventing and hair growth promoting activities.

The composition for preventing hair loss or promoting hair growth of the present invention may be prepared as a pharmaceutical composition or a cosmetic composition.

According to another aspect of the present invention, the present invention provides a method for alleviating or treating leukoderma, the method comprising administering, to a subject, the composition containing, as an active ingredient, the peptide composed of an amino acid sequence of SEQ ID NO: 1 or SEQ ID NO: 2.

According to another aspect of the present invention, the present invention provides a method for alleviating or treating obesity, the method comprising administering, to a subject, the composition containing, as an active ingredient, the peptide composed of an amino acid sequence of SEQ ID NO: 1 or SEQ ID NO: 2.

Since the method for alleviating or treating leukoderma and the method for preventing or treating obesity of the present invention employ the foregoing composition, the overlapping contents therebetween will be omitted to avoid excessive complication of the present specification.

Advantageous Effects

Features and advantages of the present invention are summarized as follows:

(i) The present invention provides a peptide having an anti-inflammatory activity and an osteogenic differentiation promoting activity, composed of one amino acid sequence selected from the group consisting of amino acid sequences of SEQ ID NO: 1, SEQ ID NO: 2, and SEQ ID NO: 3.

(ii) The present invention provides a peptide having a hair growth promoting activity, composed of an amino acid sequence selected from the group consisting of amino acid sequences of SEQ ID NO: 1 and SEQ ID NO: 3.

(iii) The peptide composed of an amino acid sequence of SEQ ID NO: 1, SEQ ID NO: 2, or SEQ ID NO: 3 of the present invention inhibits the expression of an inflammatory cytokine and suppresses the proliferation of inflammatory cells, thereby resultantly exhibiting an anti-inflammatory activity, and increases the phosphorylation of PI3K, Smad1, Smad5, and Smad8, which are involved in osteogenesis, and increases the expression of ALP, OPG, and BSP, thereby resultantly promoting osteogenic differentiation.

(iv) The peptide composed of an amino acid sequence of SEQ ID NO: 1 or SEQ ID NO: 3 of the present invention promotes the proliferation of hair follicle cells or umbilical vein endothelial cells, increases the phosphorylation of ERK, increases the expression of PI3K, β-catenin, IGF-1, KGF, and Wnt3a, which are proteins involved in hair growth, and reduces the expression of the hair loss gene DKK-1, thereby resultantly exhibiting hair loss preventing and hair growth promoting effects.

MODE FOR CARRYING OUT THE INVENTION

Figure 1A:
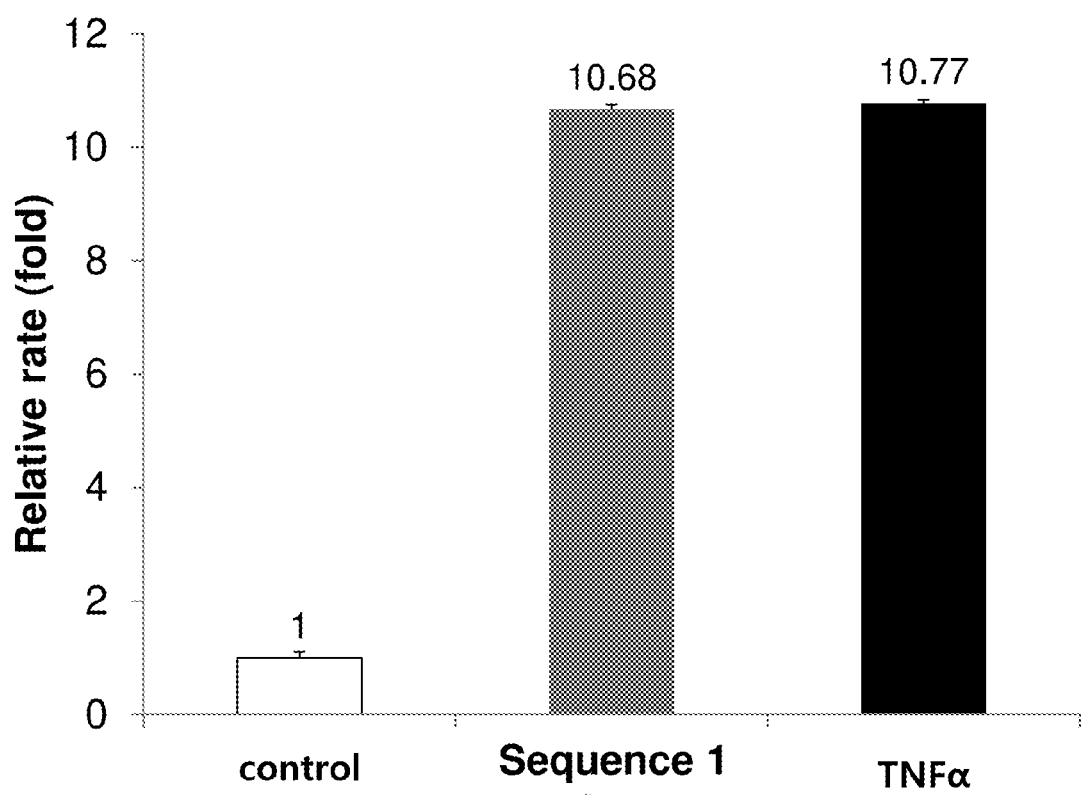
FIGS. 1a to 1c show results obtained by measuring the TNF receptor binding affinity of the peptides of the present invention.

Hereinafter, the present invention will be described in detail with reference to examples. These examples are only for illustrating the present invention more specifically, and it will be apparent to those skilled in the art that the scope of the present invention is not limited by these examples.

EXAMPLES

Synthetic Example 1: Synthesis of Peptide

To 700 mg of chloro trityl chloride resin (CTL resin, Nova Biochem Cat No. 01-64-0021) introduced into a reactor was added 10 ml of methylene chloride (MC), followed by stirring for 3 minutes. After removing the solution, 10 ml of dimethylform amide (DMF) was added, followed by stirring for 3 minutes, and then the solvent was again removed. 10 ml of a dichloromethane (DCM) solution was put into the reactor, and 200 mmole Fmoc-Cys-OH (Bachem, Swiss) and 400 mmole diisopropyl ethylamine (DIEA) were added, after which the mixture was well dissolved with stirring, and then the reaction was conducted with stirring for 1 hour. After the reaction, the resultant material was washed, and methanol and DIEA (2:1) were dissolved in DCM, followed by a reaction for 10 minutes, and then the resultant material was washed with an excessive amount of DCM/DMF (1:1). After removing the solution, 10 ml of DMF was added, followed by stirring for 3 minutes, and then the solvent was again removed. 10 ml of a deprotection solution (20% piperidine/DMF) was put in the reactor, followed by stirring at room temperature for 10 minutes, and then the solution was removed. The equal amount of a deprotection solution was added, and then the reaction was again maintained for 10 minutes, followed by removal of the solution. The resultant material was washed twice with DMF, once with MC, and once with DMF, for 3 minutes each, thereby preparing Cys-CTL resin. 10 ml of a DMF solution was put in a new reactor, and 200 mmol Fmoc-Pro (Bachem, Swiss), 200 mmol HoBt 200 mmole, and 200 mmole Bop were added, and the mixture was dissolved well through stirring. 400 mmole N,N-diisopropylethylamine (DIEA) was divisionally put twice into the reactor, and then the stirring was conducted for at least 5 minutes until all solids were dissolved. The dissolved amino acid mixed solution was put in the reactor containing the deprotected resin, followed by a reaction with stirring at room temperature for 1 hour. After removing the reaction liquid, the stirring was conducted using a DMF solution three times for 5 minutes each, followed by removal. A small amount of the reacted resin was taken to check the reaction degree by Kaiser test (Ninhydrin test). Using the deprotection solution, the deprotection reaction was conducted twice in the same manner as described above, to yield Pro-Cys-CTL resin. After sufficient washing with DMF and MC, Kaiser test was again conducted, and then the following amino acid attachment test was conducted in the same manner as described above. Based on the selected amino acid sequence, the chain reaction was conducted in the order of Fmoc-Arg(pbf), Fmoc-Gly, Fmoc-Ile, Fmoc-Ala, Fmoc-Ser(tBu), Fmoc-Arg(pbf), Fmoc-Cys(Trt) and Fmoc-Ala. The Fmoc-protective group was removed by reacting twice with the deprotection solution for 10 min each and then conducting washing well. Acetic anhydride, DIEA, and hydroxy benzotriazole (HoBt) were added to conduct acetylation for 1 hour, and then the prepared peptidyl resin was washed three times sequentially with DMF, MC, and methanol, dried under the flow of nitrogen gas, and completely dried by vacuum-drying under phosphorus pentoxide ($P_2O_5$). 30 ml of a leaving solution [95% trifluoroacetic acid (TFA), 2.5% distilled water, and 2.5% thioanisole] was added, and the reaction was maintained for 2 hours while the mixture was intermittently stirred at room temperature. The resin was filtered, washed with a small amount of a solution, and then mixed with stock solution. The distillation was conducted under reduced pressure to reduce the total volume by half, and then 50 ml of cold ether was added to induce precipitation. Thereafter, the precipitates were collected by centrifugation, followed by washing twice with cold ether. After the stock solution was removed, followed by sufficient drying under nitrogen atmosphere, thereby synthesizing 0.79 g of unpurified peptide 1, NH2-Ala-Cys-Arg-Ser-Ala-Ile-Gly-Arg-Pro-Cys-COOH (yield: 87.8%), 0.77 g of unpurified peptide 2, NH2-Ala-Cys-Phe-Thr-Arg-Thr-Ser-His-Ala-Cys-COOH (yield: 85.5%), 0.76 g of unpurified peptide 3, NH2-Ala-Cys-Asp-Gly-Arg-Thr-Gln-Ala-Leu-Cys-COOH (yield: 84.4%). The molecular weight of Peptide 1, 2 and 3 was determined as 1033.3 Da (theoretical value: 1033.2 Da), 1096.0 Da (theoretical value: 1096.2 Da) and 1036.9 Da (theoretical value: 1037.1 Da) by using a molecular weight analysis system, respectively.

TABLE 1

Sequences and Molecular Weights of Synthesized Peptides

| No. | Amino acid sequence | Analysis value (Mass spectrometer) | |
|---|---|---|---|
| | | Analytic value | Theoretical value |
| 1 | ACRSAIGRPC | 1033.3 | 1033.2 |
| 2 | ACFTRTSHAC | 1096.0 | 1096.2 |
| 3 | ACDGRTQALC | 1036.9 | 1037.1 |

Example 1: Evaluation of Anti-Inflammatory Activity 1-1. Receptor Binding Assay (TNFR)

On an ELISA plate, 50 μg/25 μl peptide and 25 μl of a coating buffer (20 mM sodium phosphate pH 9.6) were added and mixed, and then incubated at 4° C. overnight. After washing three times with PBST (300 μl), the blocking with 200 μl of a blocking buffer (3% BSA) was carried out at room temperature for 2 hours. After washing three times with PBST (300 μl), TGFR type II (R&D Systems) was added at 0.5 μg/1 ml per well, followed by incubation at room temperature for 2 hours. After washing three times with PBST (300 μl), anti-human IgG-HRP (Santa Cruz Biotechnology) was diluted at 1:1,000, which was then added at 100 μl per well, followed by incubation at room temperature for 2 hours. After washing three times with PBST (300 μl), 100 μl of TMB solution (Sigma Aldrich) was added, followed by color development. 50 μl of a stop solution (3 N $H_2SO_4$) was added to stop the reaction, and then the absorbance was read at O.D. 450 nm.

Figure 1B:
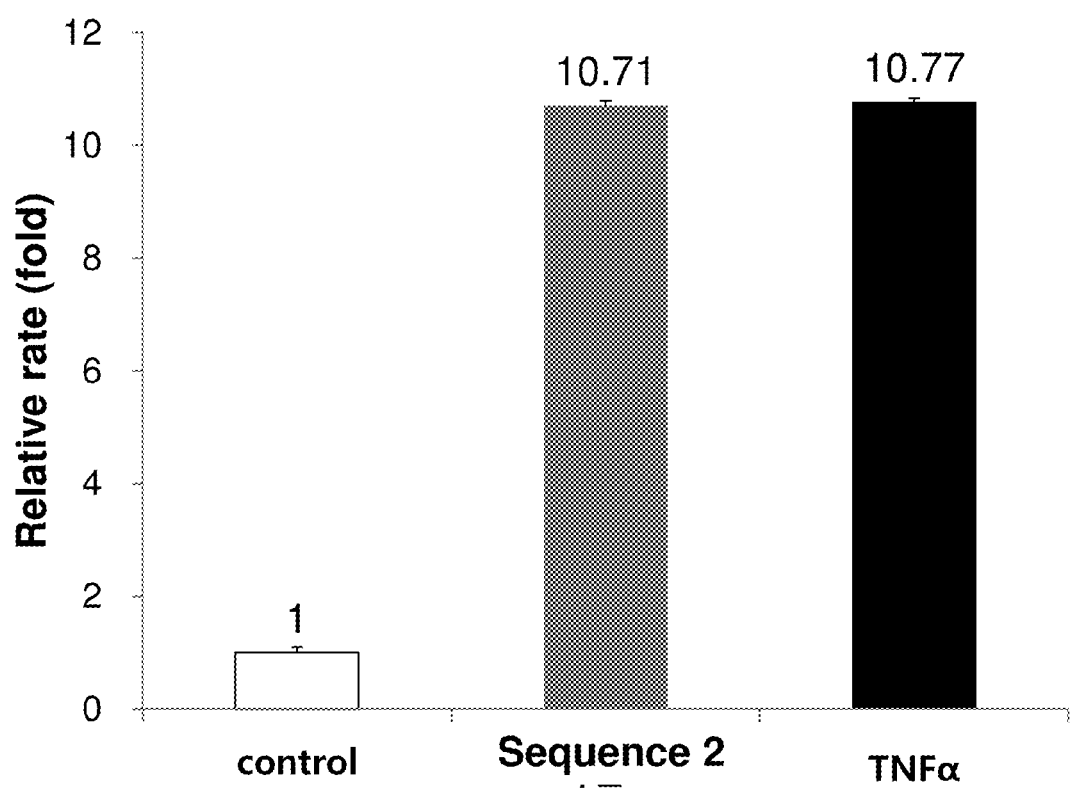
Figure 1C:
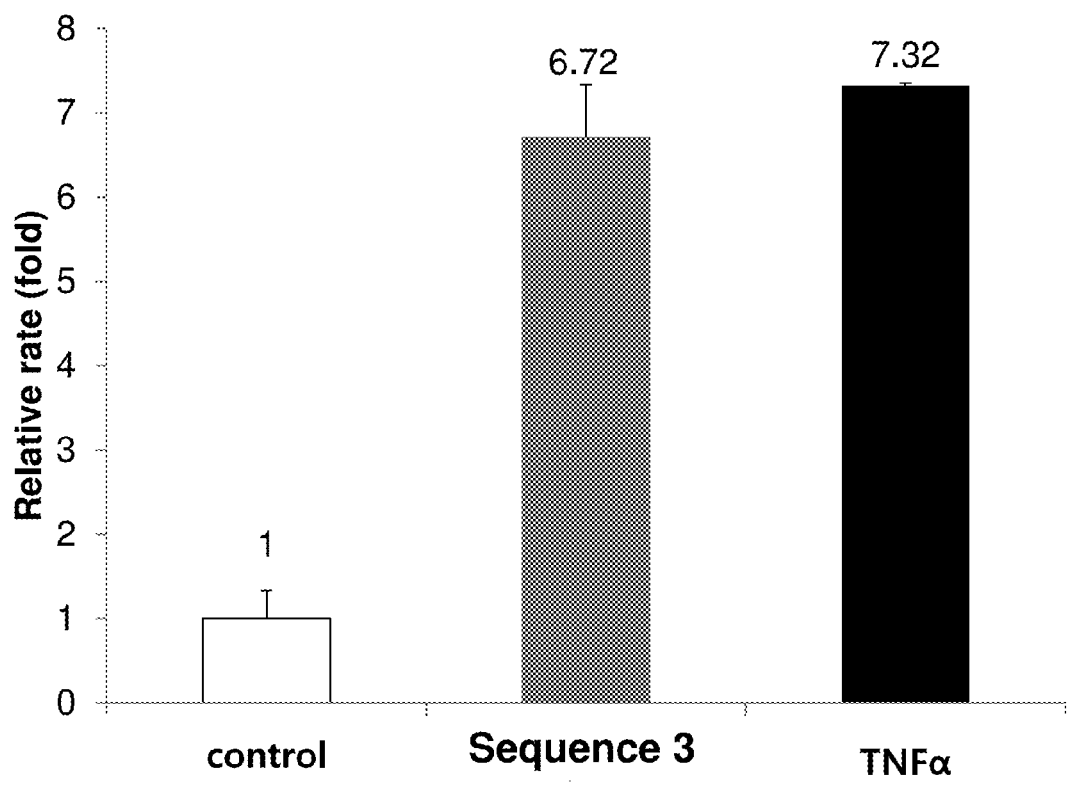
Figure 2A:
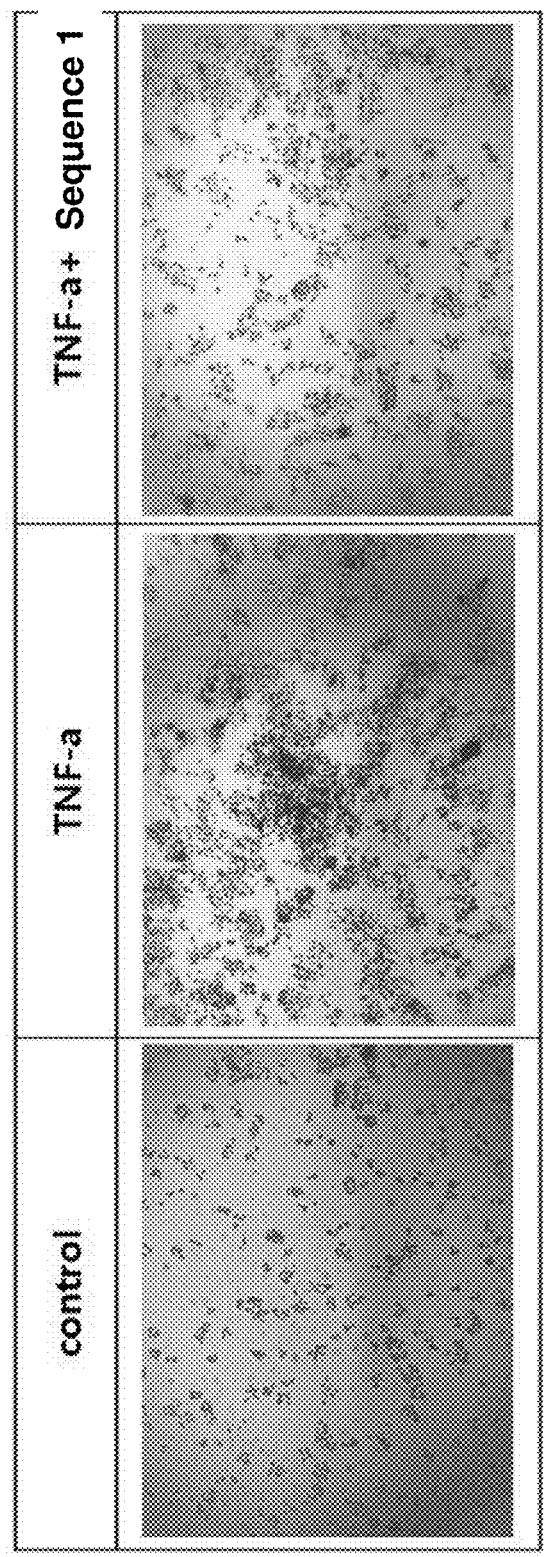
FIGS. 2a to 2f show results obtained by measuring the proliferation changes of macrophages by the peptides of the present invention.
Figure 2B:
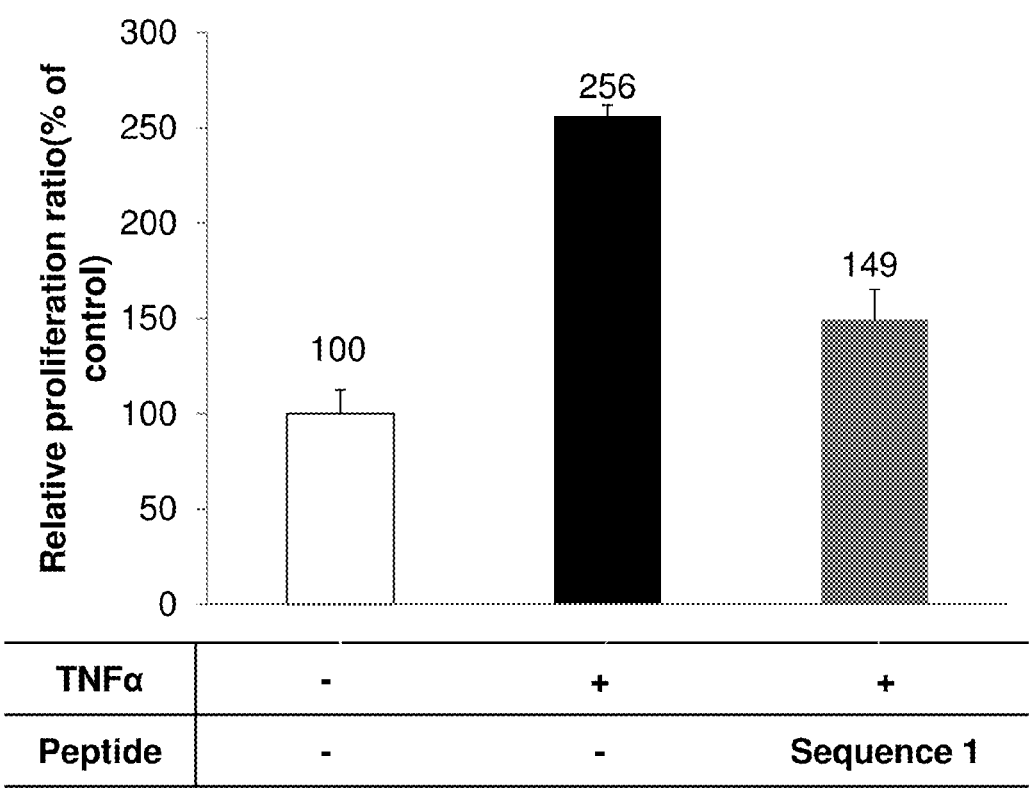
Figure 2C:
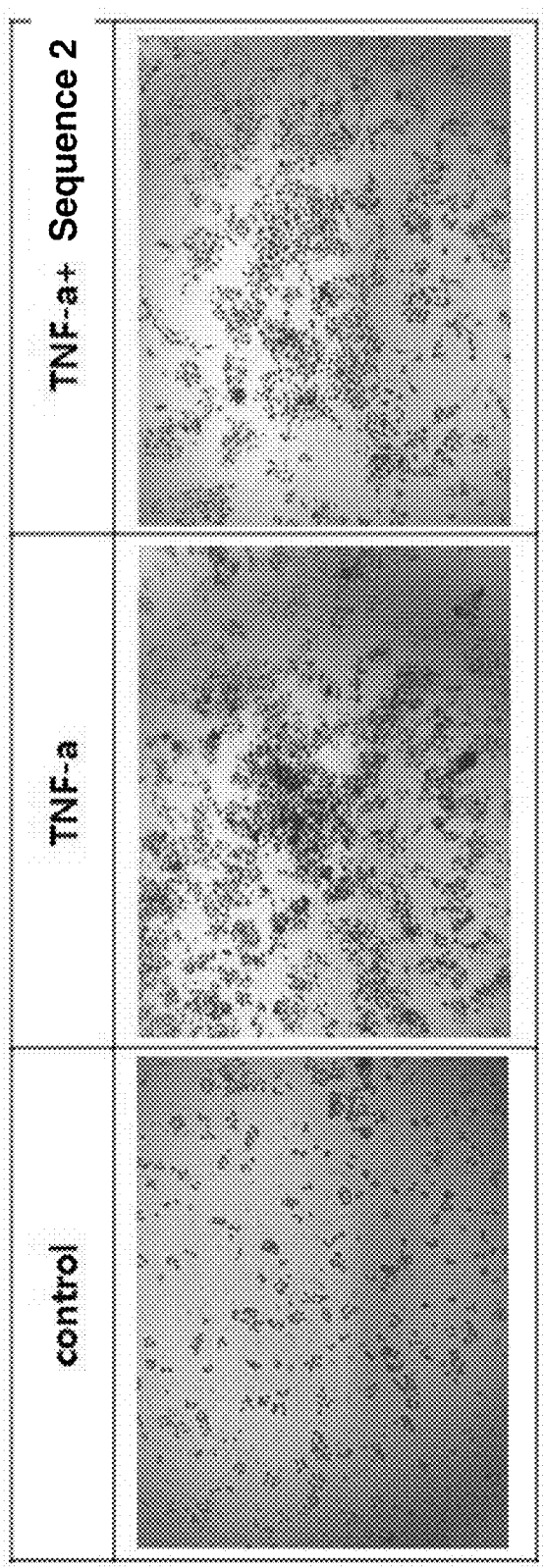
Figure 2D:
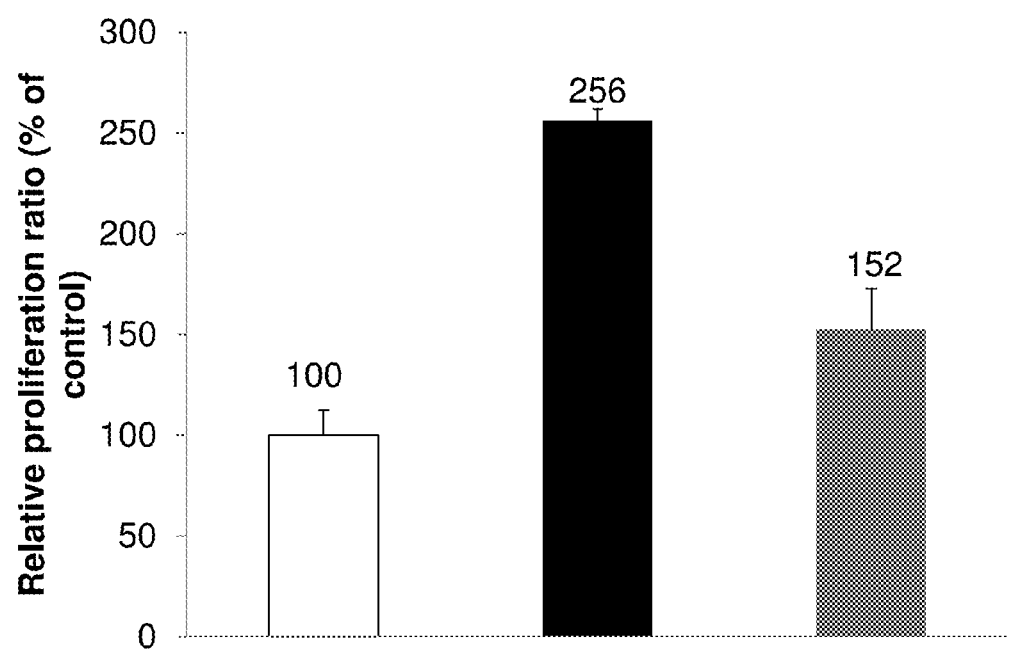
Figure 2E:
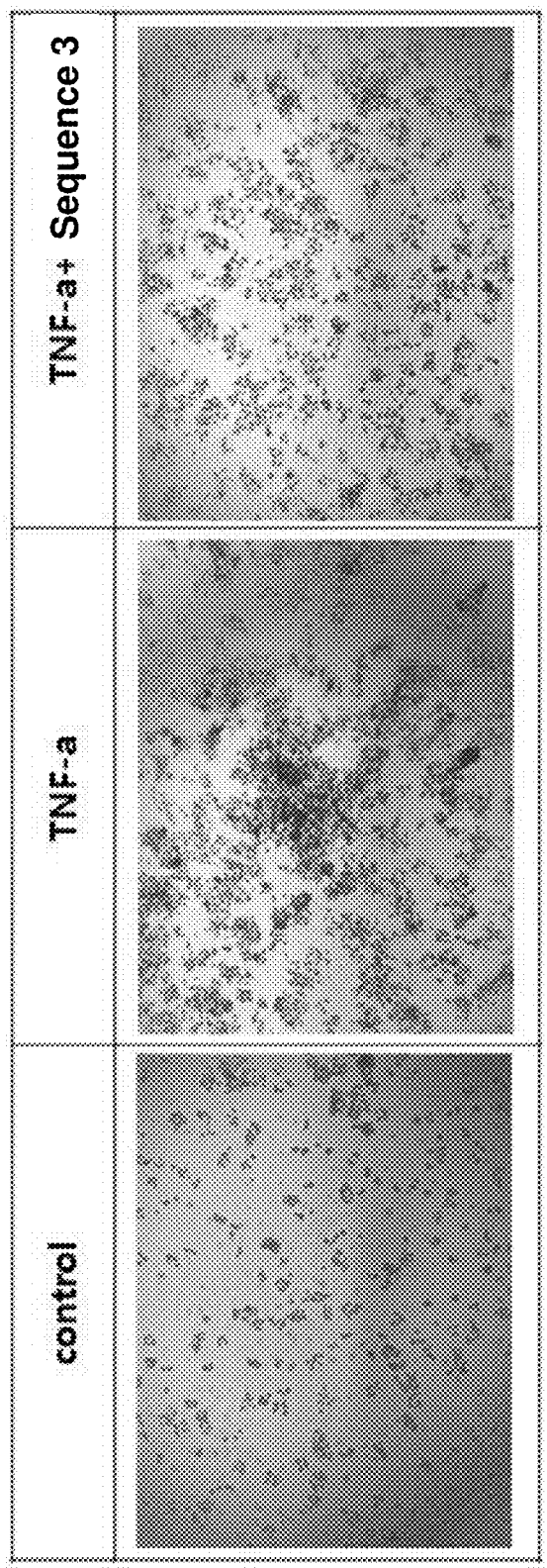
Figure 2F:
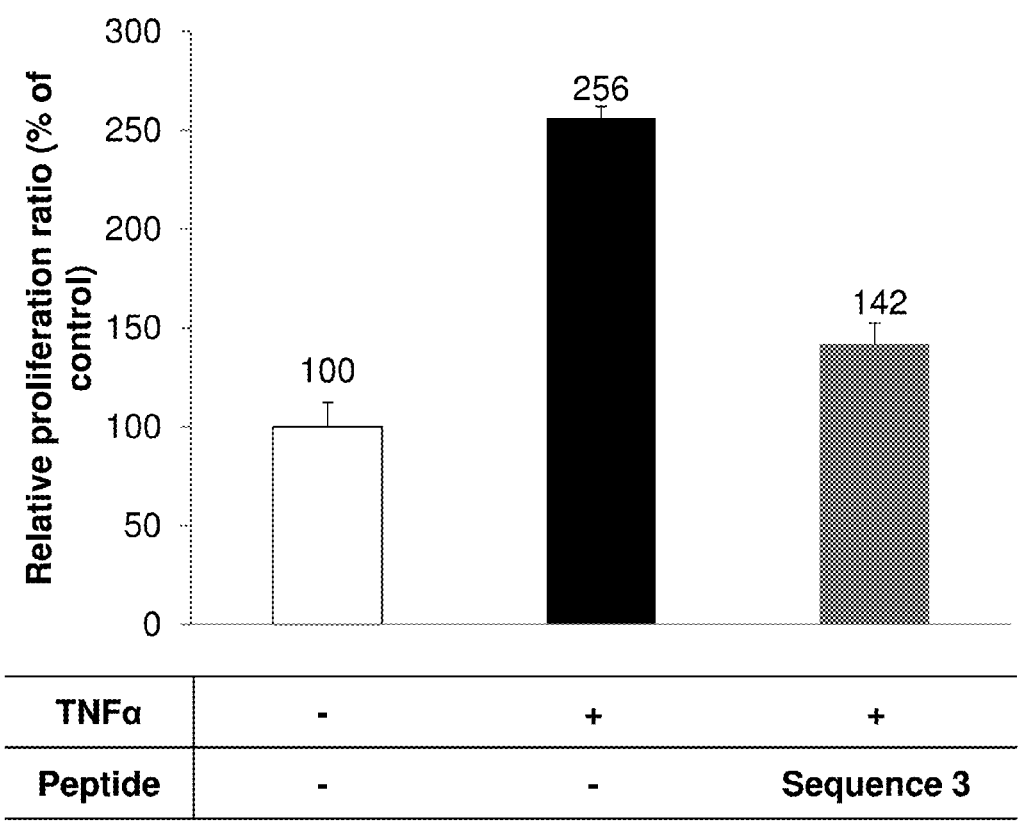

Test results verified high binding affinity of the peptides of SEQ ID NO:1, SEQ ID NO:2, and SEQ ID NO:3 to TNFR (positive control: TNF-α) (FIG. 1a-1c).

1-2. Proliferation Assay

The mouse macrophage cell line, raw 264.7 cells were seeded on a 48-well plate at a density of $1\times10^4$ cells/well. After stabilization for 24 hours, the cells were incubated in a serum-free medium for 6 hours, and then simultaneously treated with 100 ng/ml TNF-α and 50 μg/ml peptide, followed by incubation for 72 hours. After the completion of the incubation, the supernatant was removed and the cells were immobilized using ethanol, and after the cell immobilization was ended, the cells were washed three times with phosphate buffer saline (PBS). After the wash solution was removed, the cells were treated with colorimetric SRB solution, and sufficiently washed with 1% acetic acid. Then, the cells were observed using a microscope to observe the conditions of living cells. The absorbance for the solution decolorized with 20 mM tris was read at UV light of 560 nm, thereby measuring the survival conditions of cells.

Test results verified that the proliferation of RAW264.7 cells increased with TNF-α treatment was reduced by the treatment with the peptide of SEQ ID NO: 1 (FIGS. 2a-2f).

1-3. Western Blotting Using Human Hair Follicle Germinal Matrix Cells

The human hair follicle germinal matrix cells (keratinocytes), HaCaT cells were seeded on a 6-well plate at $5\times10^5$ cells/well, followed by incubation overnight, and then the cells were treated with the peptide at different concentrations, followed by incubation for 1 hour. After the cell lysis, western blotting was performed with respect to RANKL-RANK signals, p-ERK and p-c-Jun, using anti-pERK antibody (Santa Cruz Biotechnology, USA) and anti-p-c-Jun antibody (Santa Cruz Biotechnology, USA).

Figure 3A:
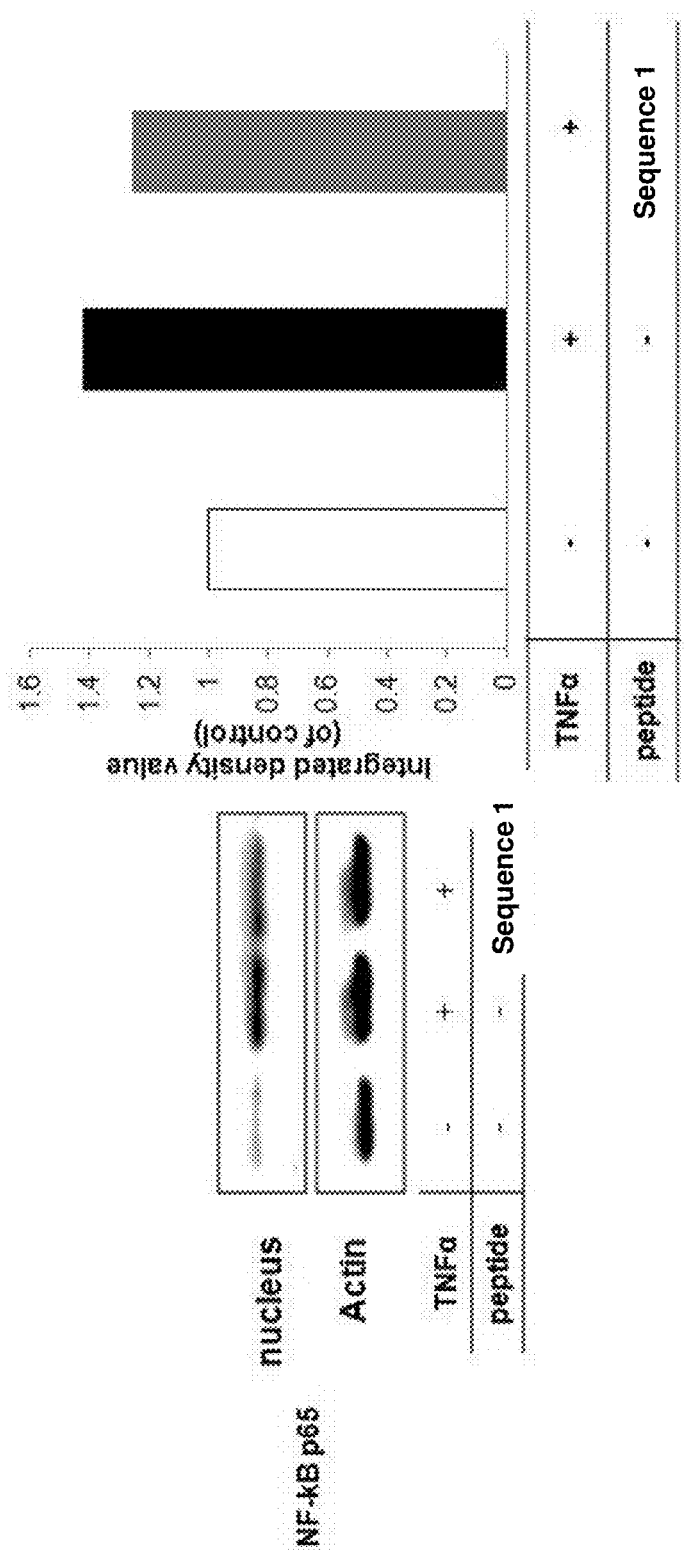
FIGS. 3a to 3c show results obtained by measuring the effects of the peptides of the present invention on the nuclear translocation of NF-κB activated by TNF-α treatment.
Figure 3B:
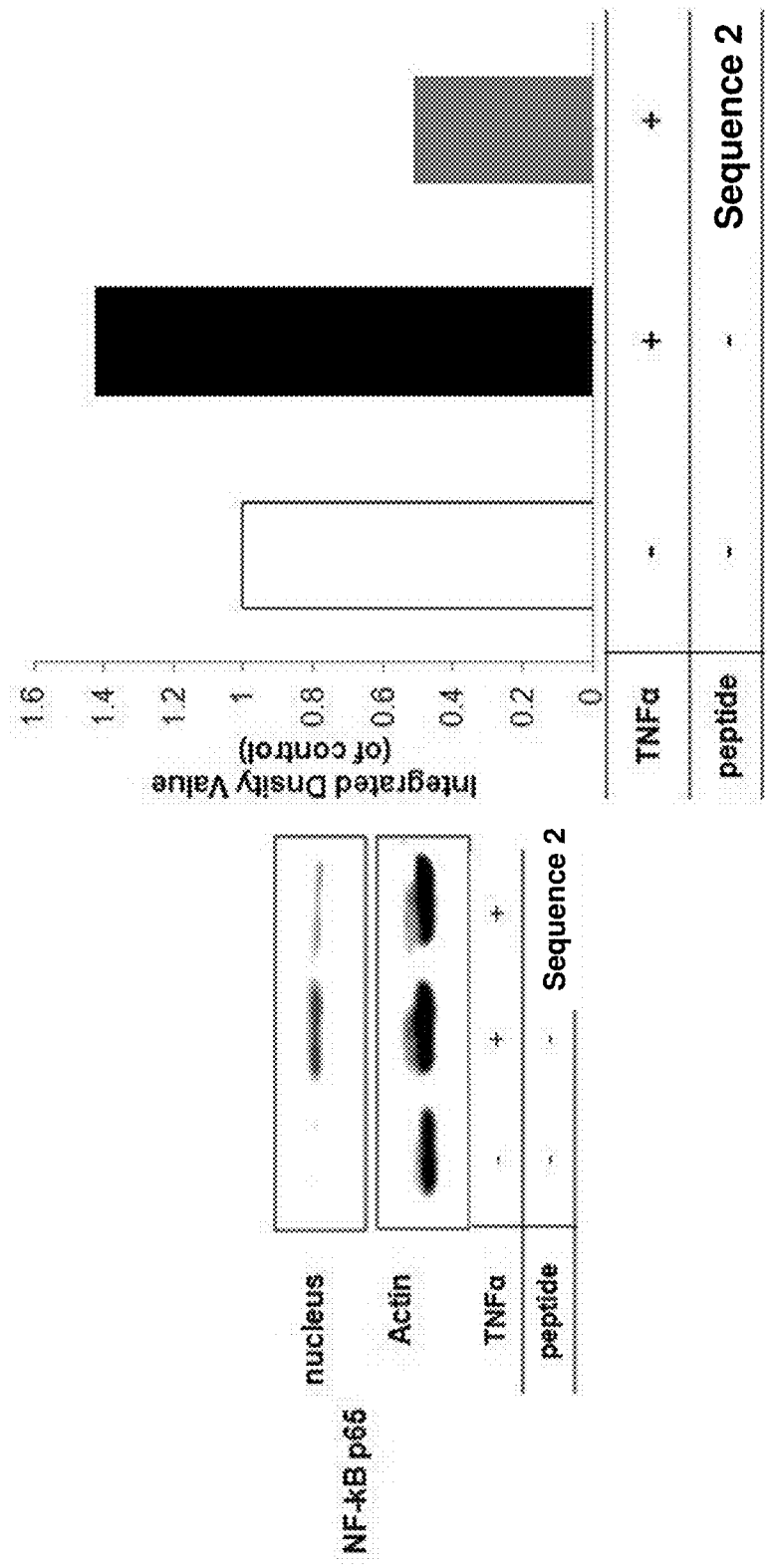
Figure 3C:
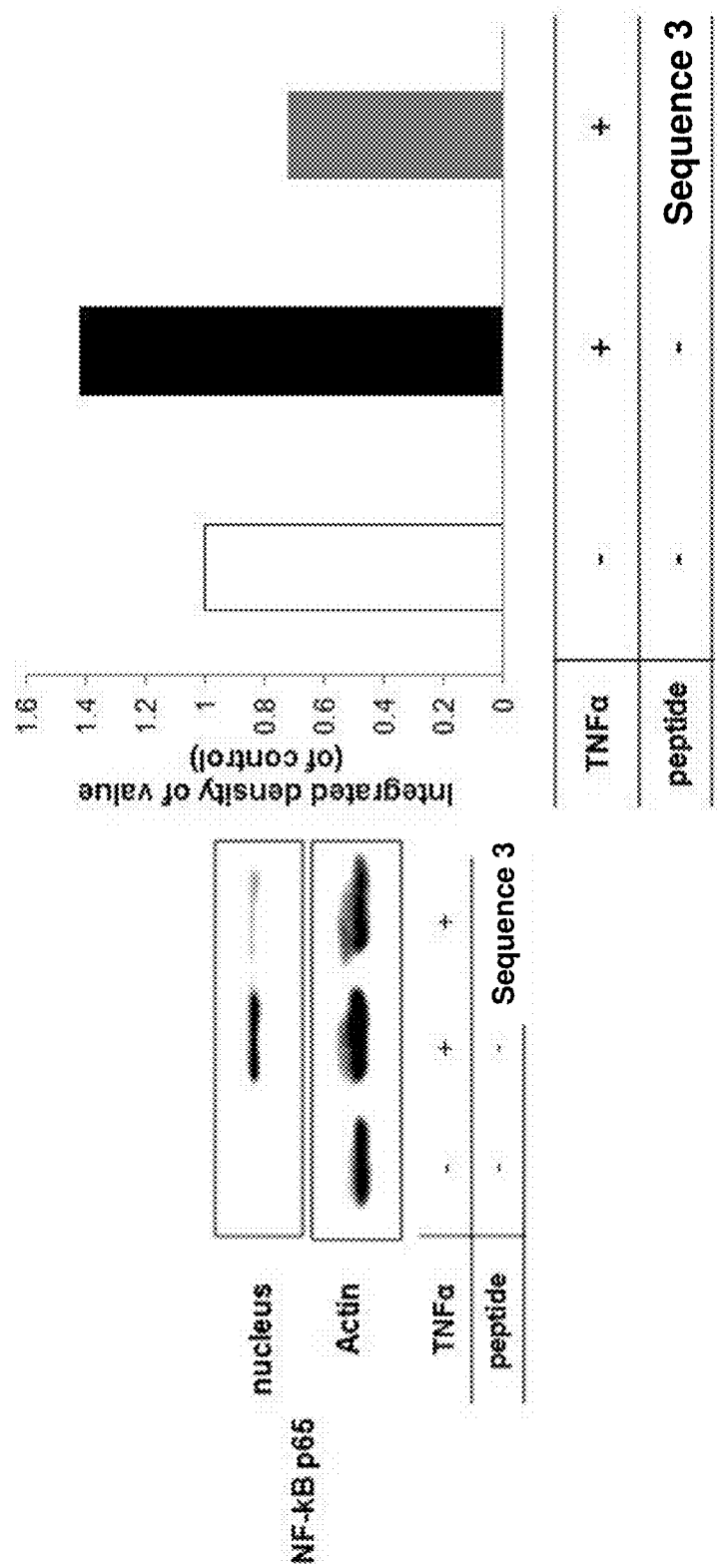
Figure 4A:
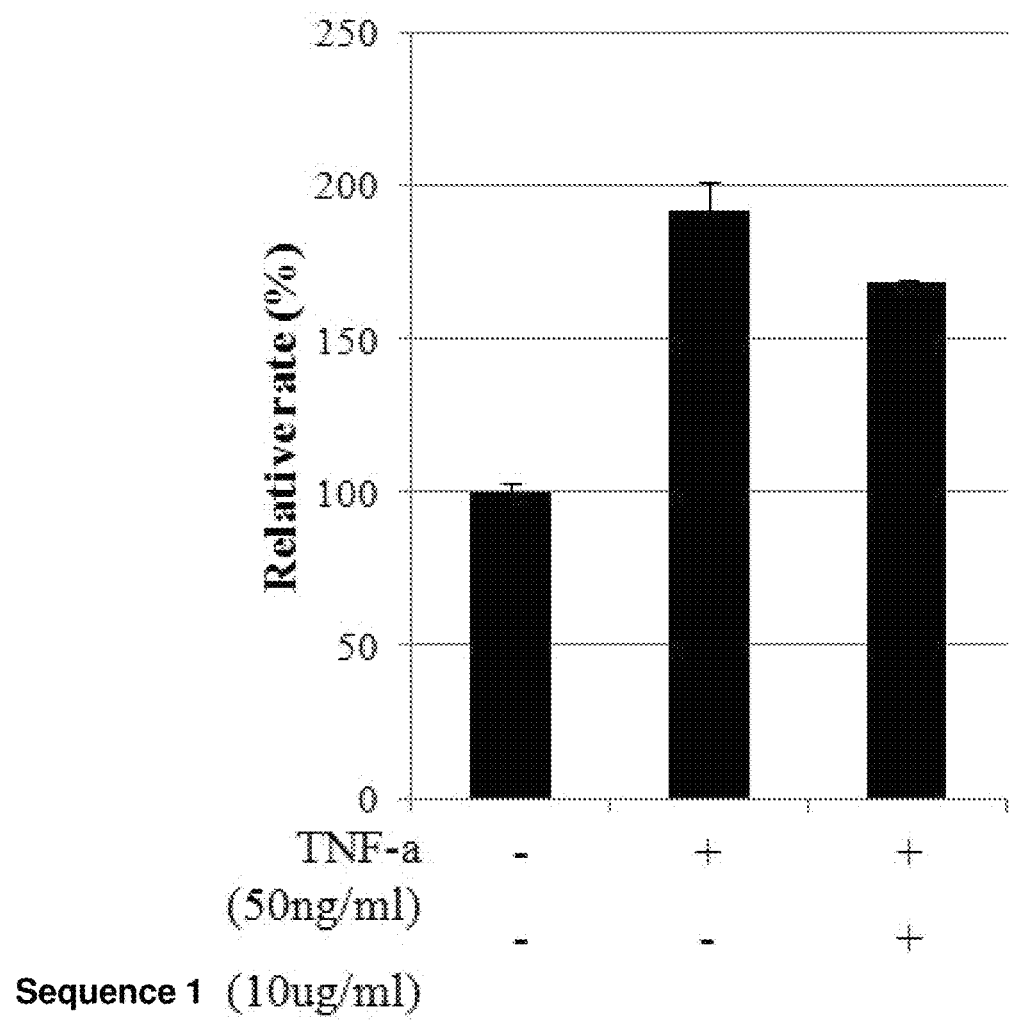
FIGS. 4a to 4c show results obtained by measuring the effects of the peptides of the present invention on the expression of IL-1β increased by TNF-α treatment.
Figure 4B:
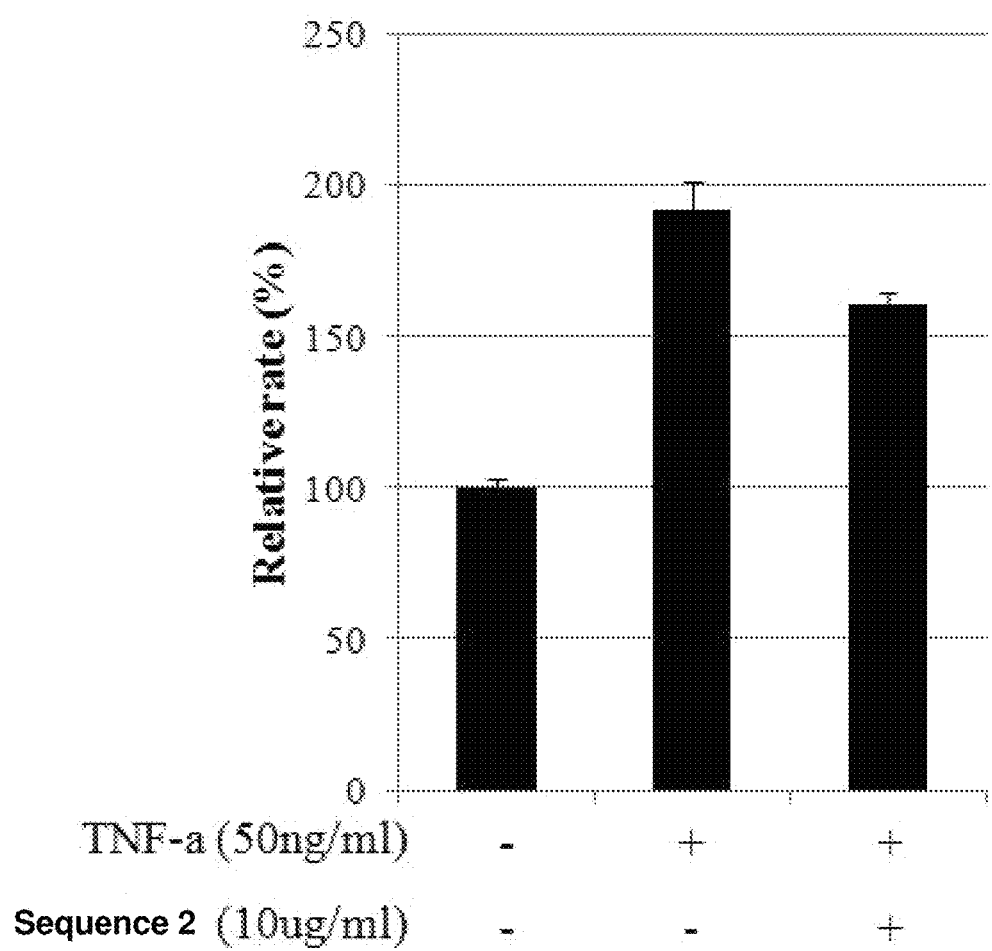
Figure 4C:
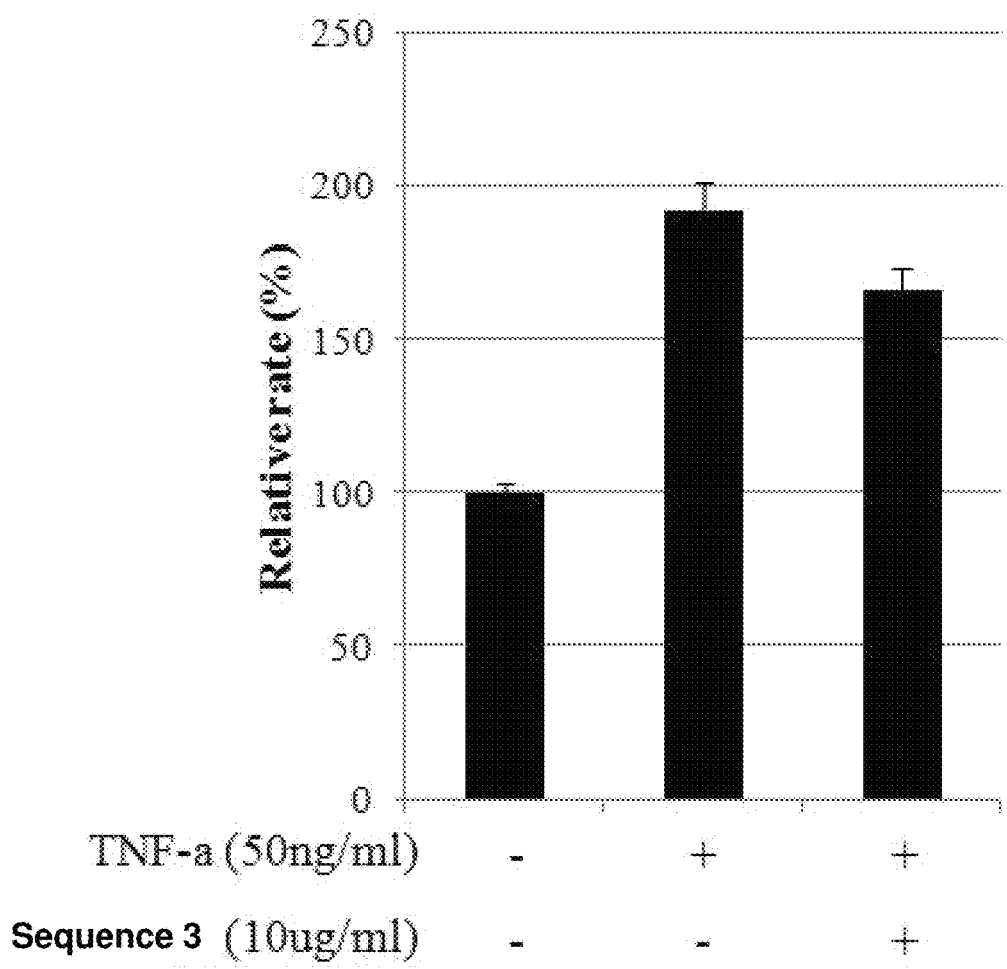
Figure 5A:
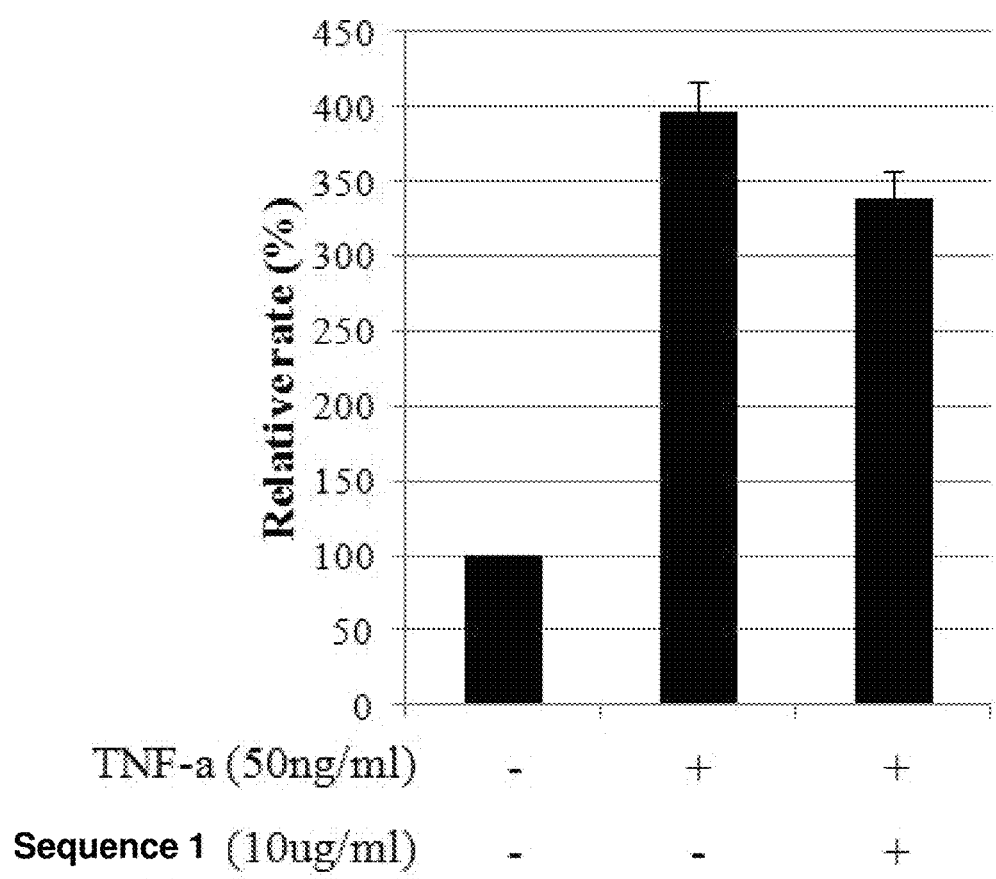
FIGS. 5a to 5c show results obtained by measuring the effects of the peptides of the present invention on the expression of IL-8 increased by TNF-α treatment.
Figure 5B:
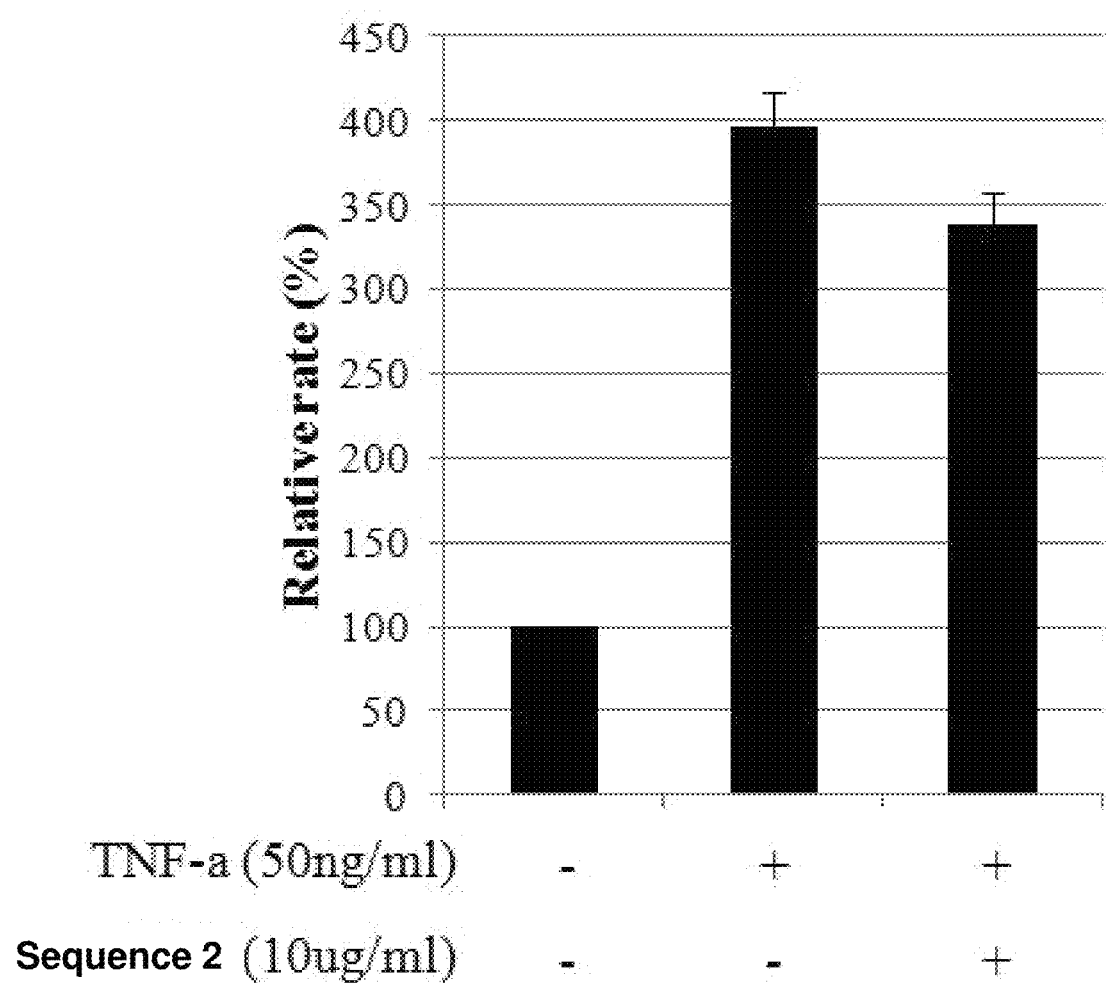
Figure 5C:
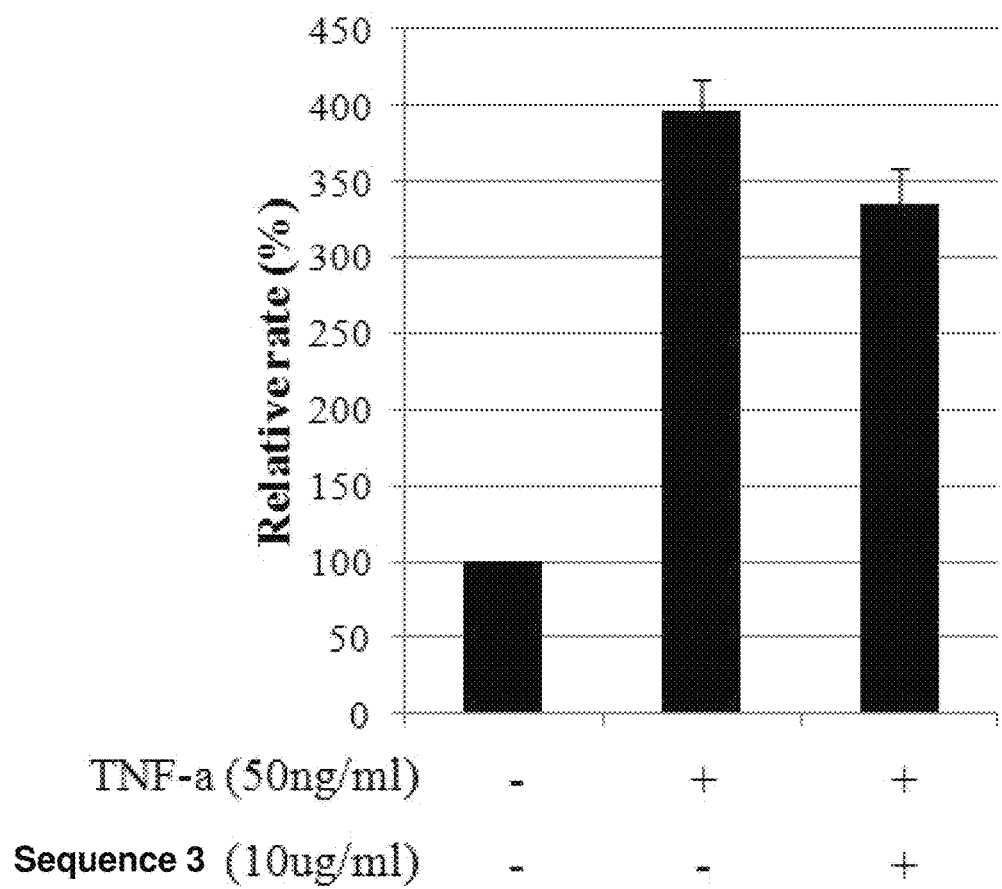

Test results verified that the nuclear translocation of NF-κB activated by TNF-α treatment was reduced by the treatment with the peptide of SEQ ID NO: 1 (FIGS. 3a-3c).

1-4. IL-1β and IL-8 ELISA

The human monocytes, THP-1 cells were seeded on a 24-well plate at a density of $2\times10^6$ cells/well. After incubation overnight, the cells were pre-treated with the samples at 10 μg/ml for 30 minutes, and treated with 50 ng/ml TNF-α, followed by incubation for 24 hours. The cell incubation medium was obtained, followed by centrifugation at 13,000 rpm for 10 minutes at 4° C., and then the supernatant was separated. ELISA was carried out using IL-1b and IL-8 ELISA kit (R&D system).

Test results verified that the expression of LI-1b and IL-8 increased by TNF-α treatment was inhibited by the treatment with the peptides of SEQ ID NO: 1, SEQ ID NO: 2, and SEQ ID NO: 3 through ELISA (FIGS. 4a-4c and 5a-5c).

Example 2: Evaluation of Osteogenic Ability 2-1. Receptor Binding Assay (HGFR)

On an ELISA plate, 50 μg/25 μl peptide and 25 μl of a coating buffer (20 mM sodium phosphate pH 9.6) were added and mixed, and then incubated at 4° C. overnight. After washing three times with PBST (300 μl), the blocking with 200 μl of a blocking buffer (3% BSA) was carried out at room temperature for 2 hours. After washing three times with PBST (300 μl), HGFR (R&D Systems) was added at 0.5 μg/1 ml per well, followed by incubation at room temperature for 2 hours. After washing three times with PBST (300 μl), anti-human IgG-HRP was diluted at 1:1,000, which was then added at 100 μl per well, followed by incubation at room temperature for 2 hours. After washing three times with PBST (300 μl), 100 μl of TMB solution was added, followed by color development. 50 μl of a stop solution (3 N $H_2SO_4$) was added to stop the reaction, and then the absorbance was read at O.D. 450 nm.

Figure 6:
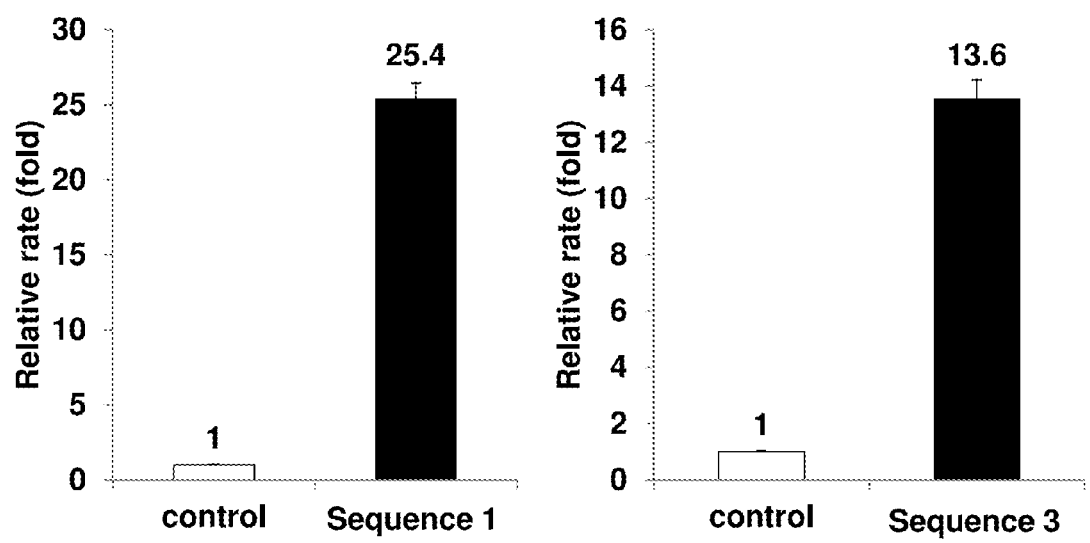
FIG. 6 shows results obtained by measuring the HGF receptor binding degrees of the peptides of the present invention.

Test results verified high binding affinity of the peptides of SEQ ID NO: 1 and SEQ ID NO: 3 on HGFR (FIG. 6).

2-2. Western Blotting Using Osteoblasts (PI3K Phosphorylation)

MC313-E1 (mouse osteoblast line) cells were seeded on a 6-well plate at a cell density of $2\times10^5$ cells/well, and then the cells incubated overnight were incubated in a serum-free medium for 24 hours. The cells were treated with the peptides at 50 μg/ml for 15 minutes (positive control: HGF 50 ng/ml). The cells were treated with the cell lysis buffer to obtain a lysate, followed by protein quantification, and then western blotting was performed with respect to Phospho-PI3K (P-PI3K) using anti-pPI3K antibody (Santa Cruz Biotechnology, USA).

Figure 7:
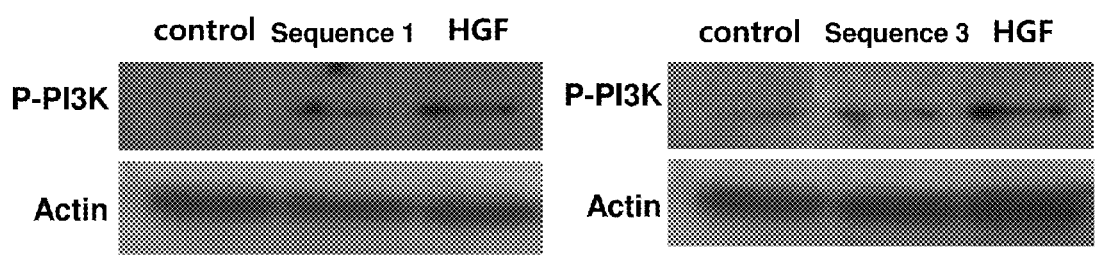
FIG. 7 shows results obtained by measuring the effects of the peptides of the present invention on the phosphorylation of PI3K increased by HGF receptor signal stimulation.

It could be verified that the treatment with the peptides of SEQ ID NO: 1 and SEQ ID NO: 3, exhibiting high binding affinity to HGFR, increased the phosphorylation of PI3K by HGFR signal stimulation (FIG. 7).

2-3. Receptor Binding Assay (BMPR)

In an ELISA plate, 50 μg/25 μl peptide and 25 μl of a coating buffer (20 mM sodium phosphate pH 9.6) were added and mixed, and then incubated at 4° C. overnight. After washing three times with PBST (300 μl), the blocking with 200 μl of a blocking buffer (3% BSA) was carried out at room temperature for 2 hours. After washing three times with PBST (300 μl), BMPR-IB (R&D Systems) was added at 0.5 μg/1 ml per well, followed by incubation at room temperature for 2 hours. After washing three times with PBST (300 μl), anti-human IgG-HRP was diluted at 1:1,000, which was then added at 100 μl per well, followed by incubation at room temperature for 2 hours. After washing three times with PBST (300 μl), 100 μl of TMB solution was added, followed by color development. 50 μl of a stop solution (3 N $H_2SO_4$) was added to stop the reaction, and then the absorbance was determined at O.D. 450 nm.

Figure 8:
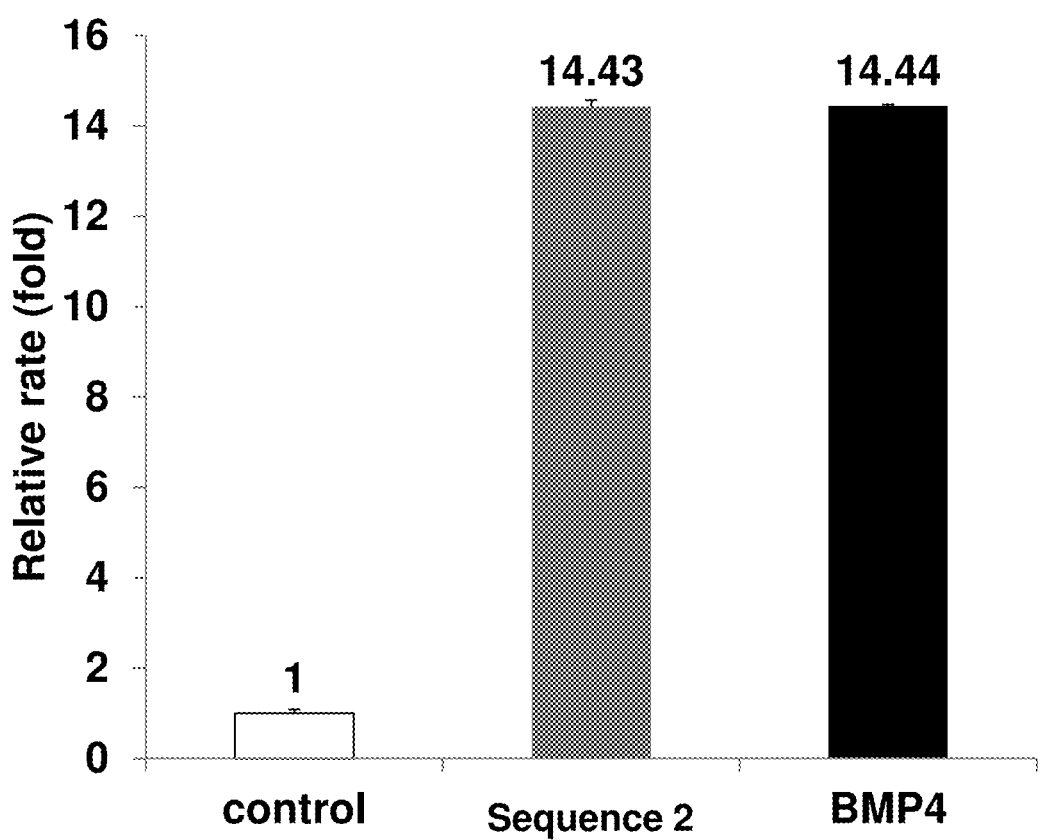
FIG. 8 shows results by measuring the BMP receptor binding degree of the peptide of the present invention.

Test results verified high binding affinity of the peptide of SEQ ID NO: 2 on BMPR (positive control: BMP4) (FIG. 8).

2-4. Western Blotting Using Osteoblasts (Smad1/5/8 Phosphorylation)

MC313-E1 (mouse osteoblast line) cells were seeded on a 6-well plate at a cell density of $2\times10^5$ cells/well. The cells incubated overnight were incubated in a serum-free medium for 24 hours, and then treated with the peptide at 50 μg/ml for 15 minutes and 30 minutes (positive control; BMP4 50 ng/ml). The cells were treated with the cell lysis buffer to obtain a lysate, followed by protein quantification, and then western blotting was performed with respect to Phospho-smad1/5/8 (P-smad1/5/8) using anti-p-smad1/5/8 antibody (Santa Cruz Biotechnology, USA).

Figure 9:
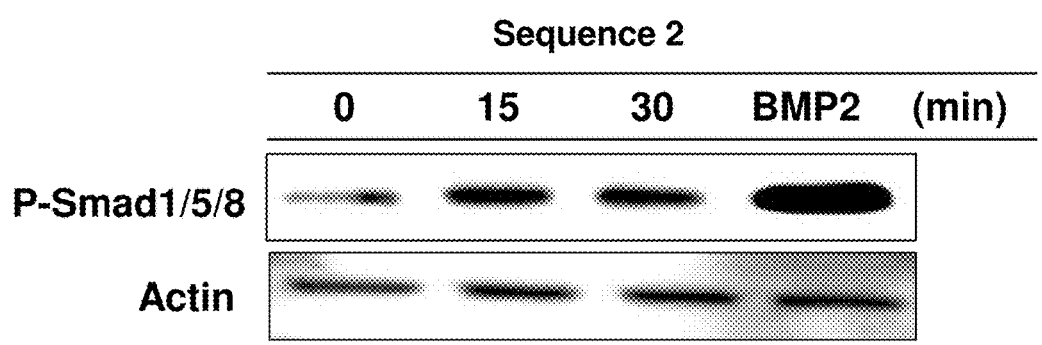
FIG. 9 shows results obtained by measuring the effect of the peptide of the present invention on the phosphorylation of Smad1/5/8 increased by BMP receptor signal stimulation.

It could be verified that the treatment with the peptide of SEQ ID NO: 2, exhibiting high binding affinity to BMPR, increased the phosphorylation of Smad1/5/8 by BMPR signal stimulation (FIG. 9).

2-5. ALP Staining

The mouse osteoblast line, MC3T3-E1 cells were seeded on a 24-well plate at $4\times10^4$ cells/well, and then incubated overnight. After the exchange with a medium containing 50 μg/ml ascorbic acid+10 mM b-glycerophosphate, the cells were treated with each peptide at concentrations of 10 μg/ml and 50 μg/ml, and incubated for 14 days to induce differentiation. Here, the medium exchange every three days and the treatment with the peptide were repeated (positive control: BMP2 ng/ml). The incubation-completed plate well was washed two times with PBS, and then the cells were immobilized with an immobilization buffer, in which acetone, 37% formaldehyde, and citric acid solution were mixed, for 30 seconds. The following staining was carried out using the leukocyte alkaline phosphatase staining kit (SIGMA).

The cells were treated with a mixture, in which an FBB-alkaline solution was mixed with a sodium nitrite solution at 1:1, for 2 minutes, and then treated with a buffer composed of distilled water and naphthol AS-BI alkaline solution, followed by color development in an incubator at 37° C. for 1 hour.

Figure 10A:
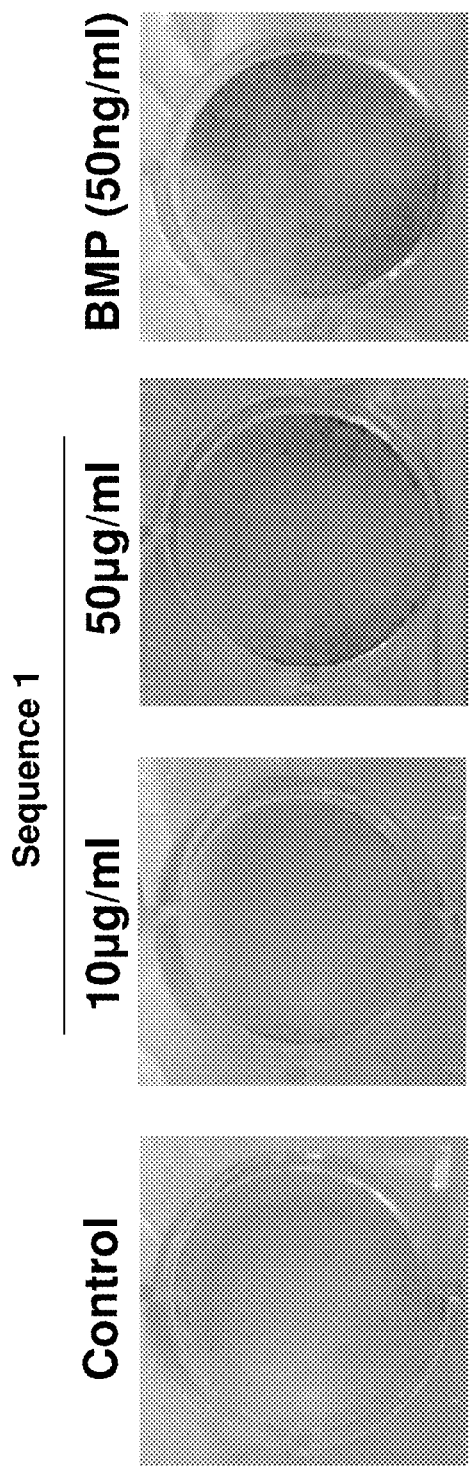
FIGS. 10a to 10c show results obtained by measuring the ALP expression changes of the peptides of the present invention.
Figure 10B:
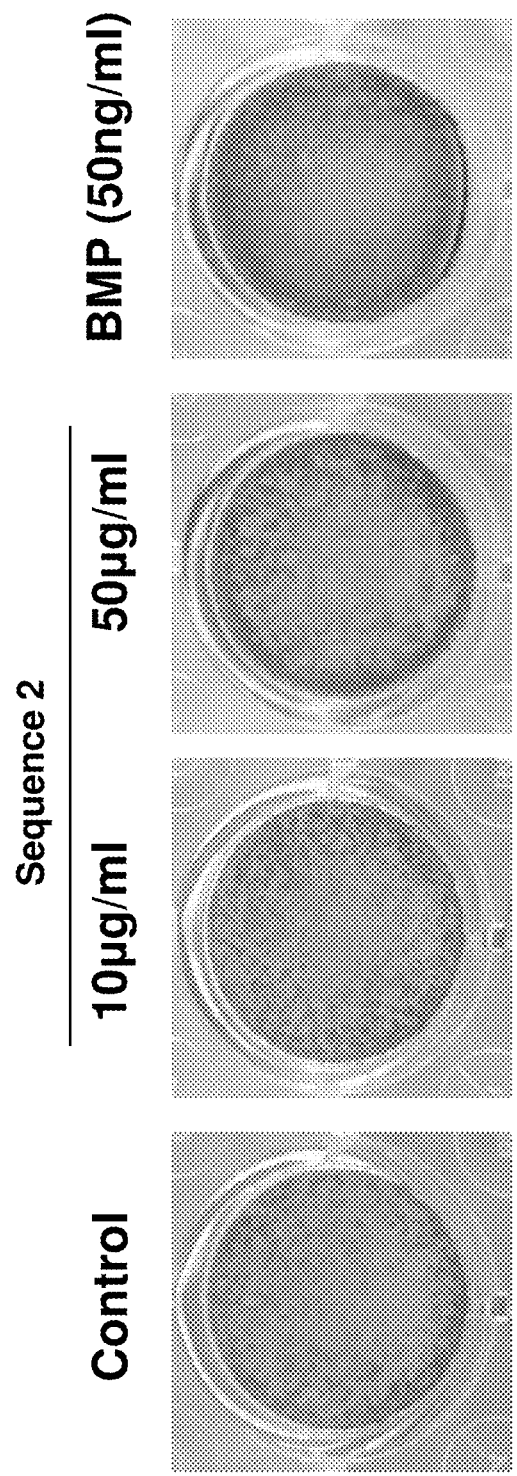
Figure 10C:
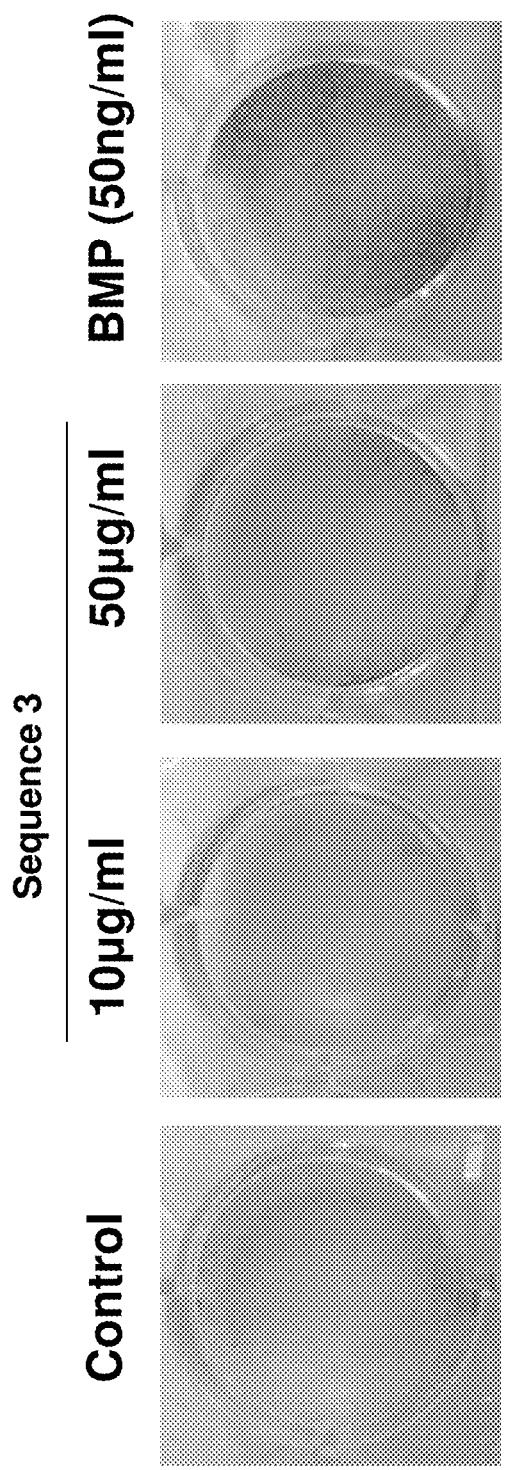

Test results verified that the treatment of pre-osteoblasts MC3T3-E1 with the peptide of SEQ ID NO: 1 at different concentrations increased the ALP expression through the promotion of differentiation (FIGS. 10a-10c).

2-6. Alizarin Red Staining

MC3T3-E1 (mouse osteoblast line) cells were seeded on a 24-well plate at a cell density of $4 \times 10^4$ cells/well. The medium of cells incubated overnight was exchanged with α-MEM medium containing 50 μg/ml ascrobic acid and mM β-glycerophosphate, and then the cells were treated with the peptides at different concentrations (10 and 50 μg/ml), followed by incubation in an incubator at 37° C. for 14 days. Here, the medium exchange every three days and the treatment with the peptide were repeated (positive control: 30 ng/ml rhBMP2 (Cell signaling)). After the completion of the incubation, the plate well was washed two times with PBS, and the cells were immobilized by the treatment with 70% EtOH for 1 hour. Then, the cells were stained with 40 mM Alizarin red S (pH 4.2, Sigma Aldrich) for 10 minutes. The cells were treated with 10% cetyl pyridinium chloride (dissolved in 10 mM sodium phosphate (pH 7.0)) for 15 minutes, and then the absorbance was read at 560 nm using a spectrophotometer (SpectraMax, Molecular Devices).

Figure 11A:
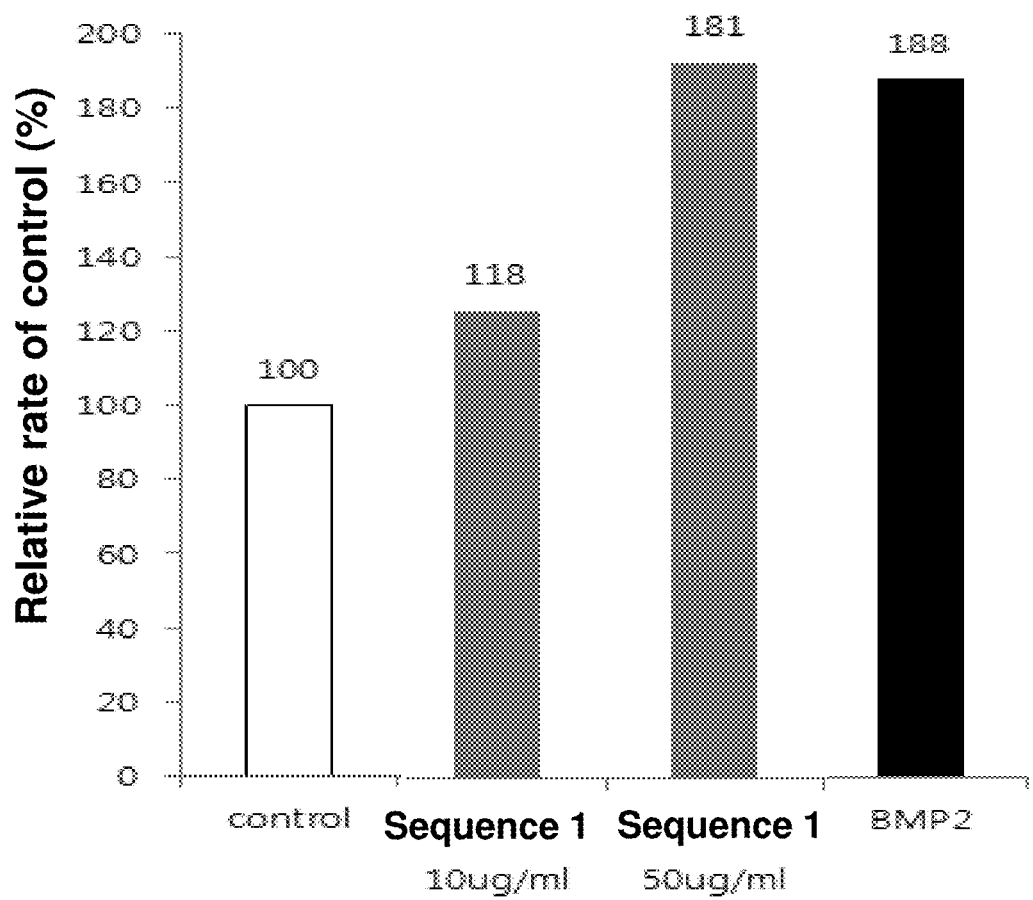
FIGS. 11a to 11c show results obtained by measuring the mineralization by the promotion of osteogenic differentiation of the peptides of the present invention.
Figure 11B:
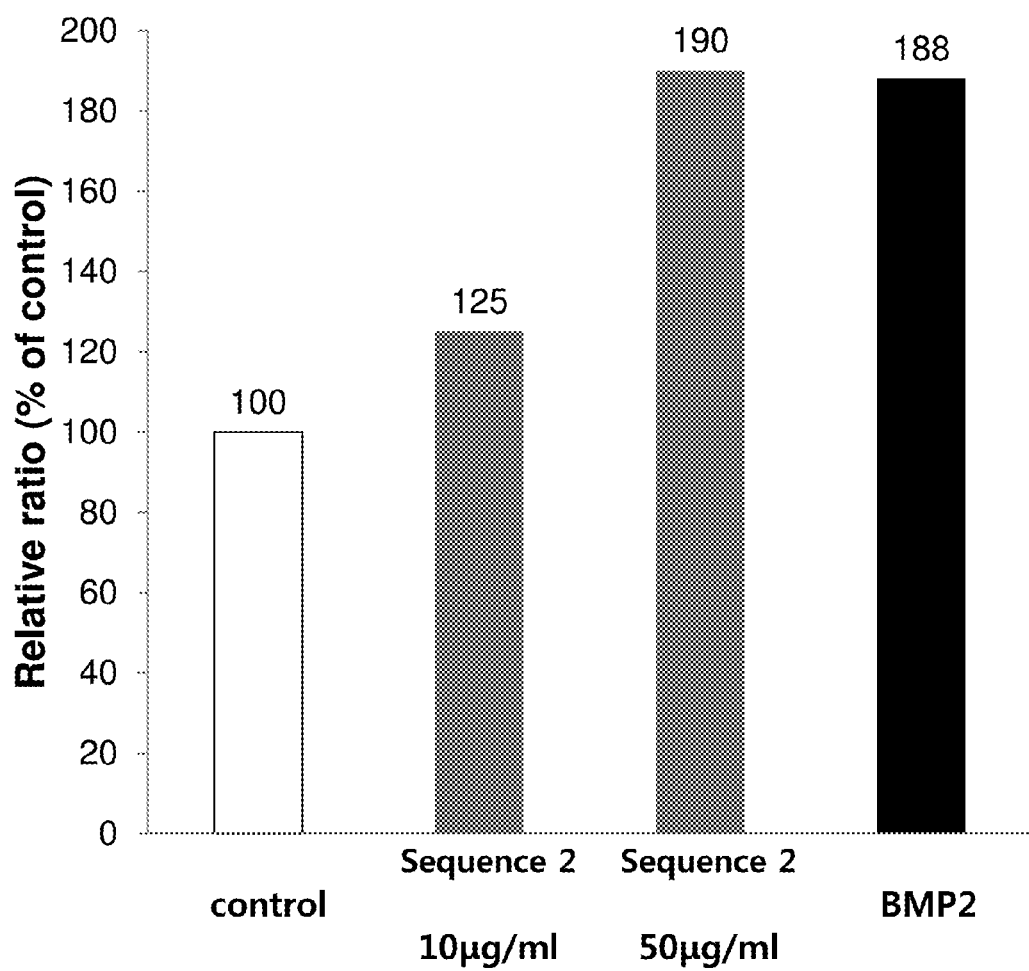
Figure 11C:
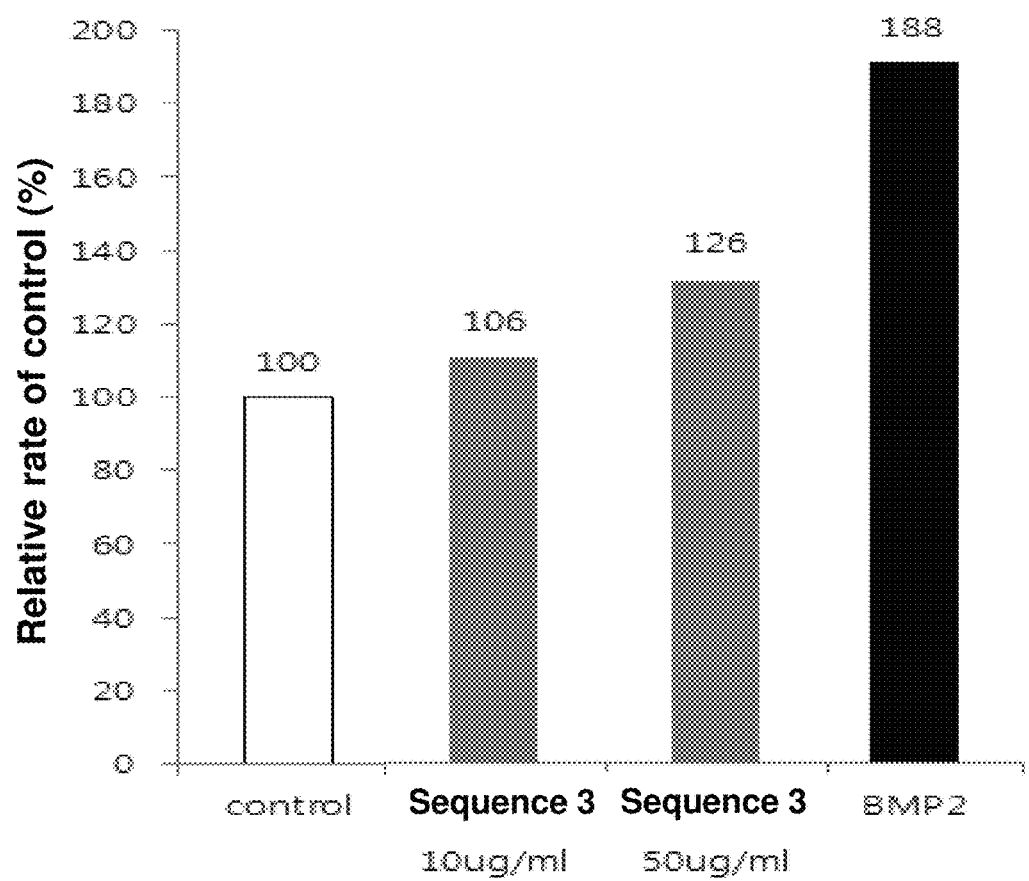

It was verified through Alizarin red staining that the treatment of pre-osteoblasts MC3T3-E1 with the peptide of SEQ ID NO: 1 at different concentrations increased the mineralization through the promotion of differentiation (FIGS. 11a-11c).

2-7. RT-PCR

MC3T3-E1 (mouse osteoblast line) cells were seeded on a 6-well plate at a cell density of $1 \times 10^5$ cells/well. The cells incubated overnight were treated with the peptides at different concentrations (10 and 50 μg/ml), followed by incubation in an incubator at 37° C. for three days (positive control: 100 ng/ml BMP2 (Cell signaling)). After the incubation-completed cells were collected, the cells were treated with RNA extraction solution (Easy Blue, Intron) to prepare RNA, and then cDNA was synthesized using RT pre-mix (Intron). PCR was carried out using primers of respective markers (OPG, ALP, BSP) and PCR pre-mix (Intron).

Target-specific primer sequences used in PCR for osteogenic differentiation markers were as follows: OPG forward primer sequence, 5'-CTGCCTGGGAAGAAGATCAG-3' and OPG reverse primer, 5'-TTGTGAAGCTGTGCAGGAAC-3' (annealing temperature, 60° C.); ALP forward primer sequence, 5'-CCAGCAGGTTTCTCTCTTGG-3' and ALP reverse primer, 5'-CTGGGAGRCRCATCCTGAGC-3' (annealing temperature, 60° C.); BSP forward primer sequence, 5'-AAAGTGAAGGAAAGCGACGA-3' and BSP reverse primer, 5'-GTTCCTTCTGCACCTGCTTC-3' (annealing temperature, 60° C.)

5 μl of PCR product was loaded on 1% agarose gel, followed by electrophoresis, and then the bands were investigated using Gel-Doc.

Figure 12A:
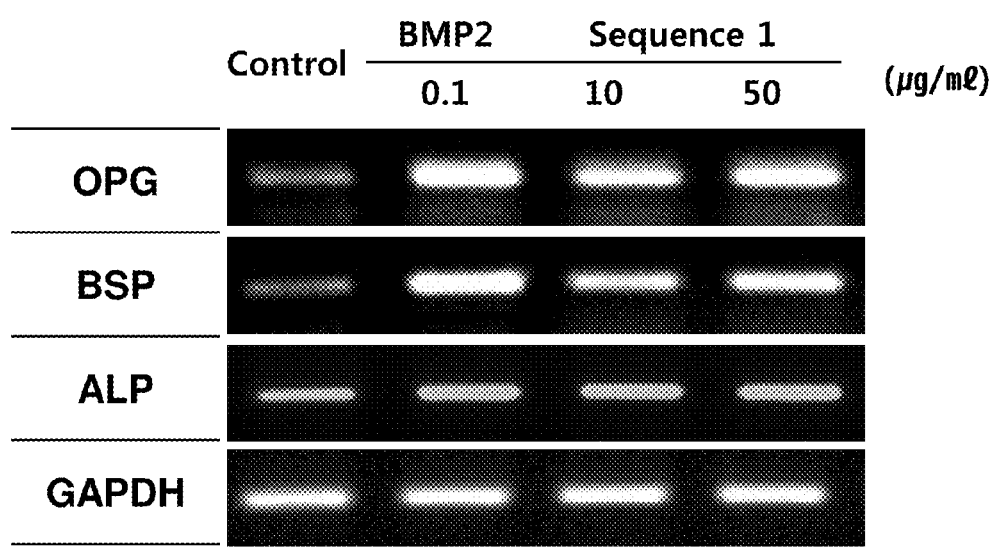
FIGS. 12a to 12c show results obtained by measuring the changes in the expression of osteogenic differentiation markers (OPG, ALP, and BSP) by the peptides of the present invention.
Figure 12B:
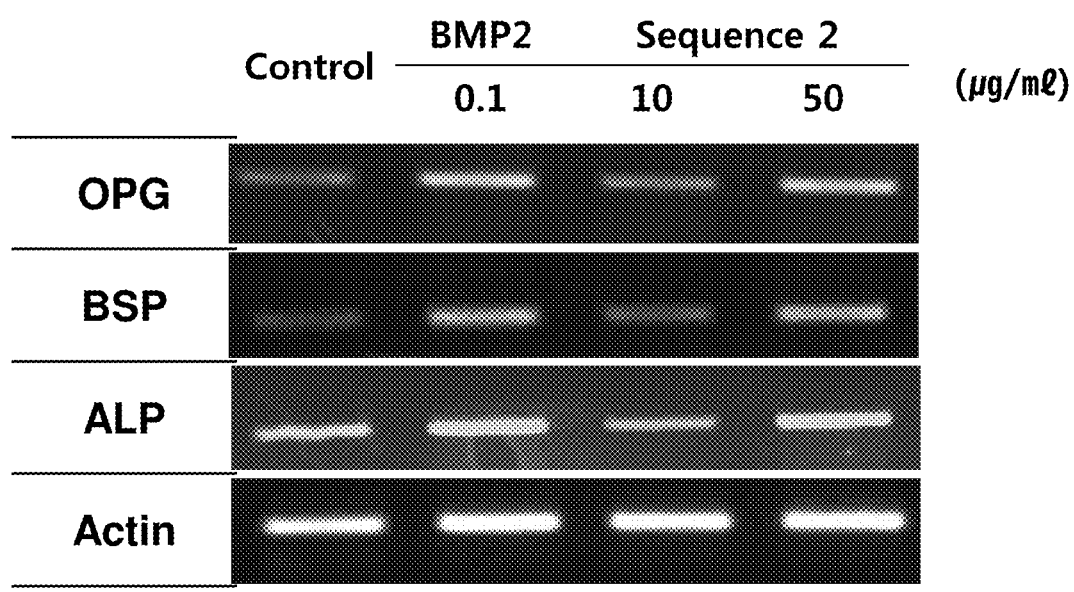
Figure 12C:
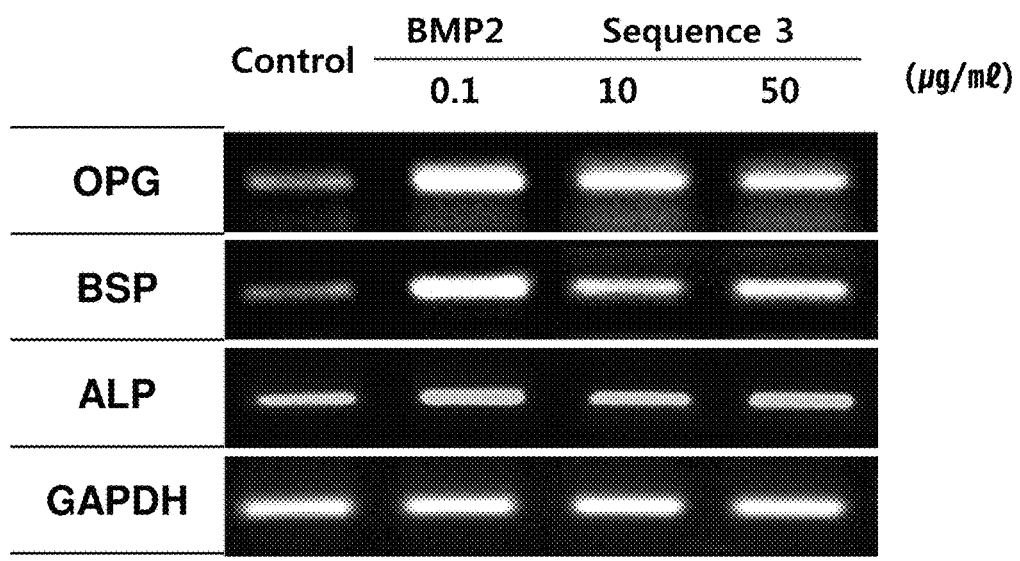
Figure 13A:
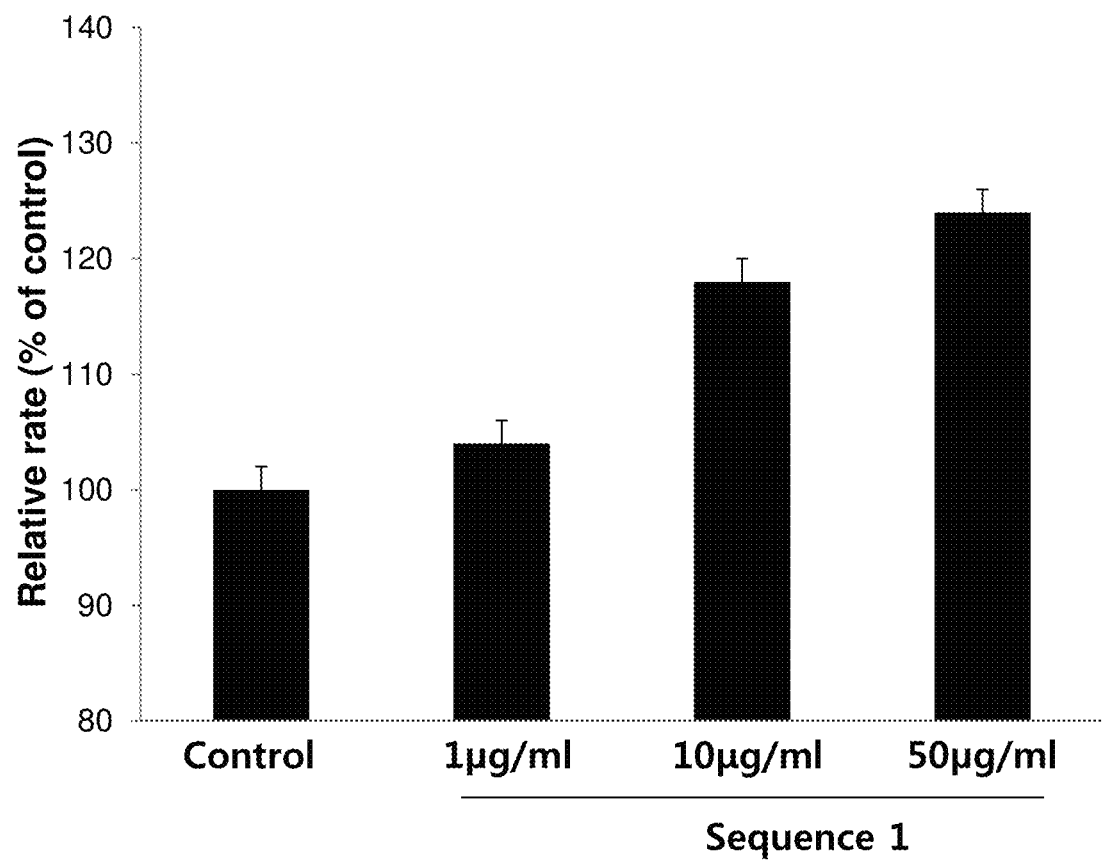
FIGS. 13a and 13b show results obtained by measuring the change in the proliferation of human hair follicle dermal papilla cells by the peptides of the present invention.
Figure 13B:
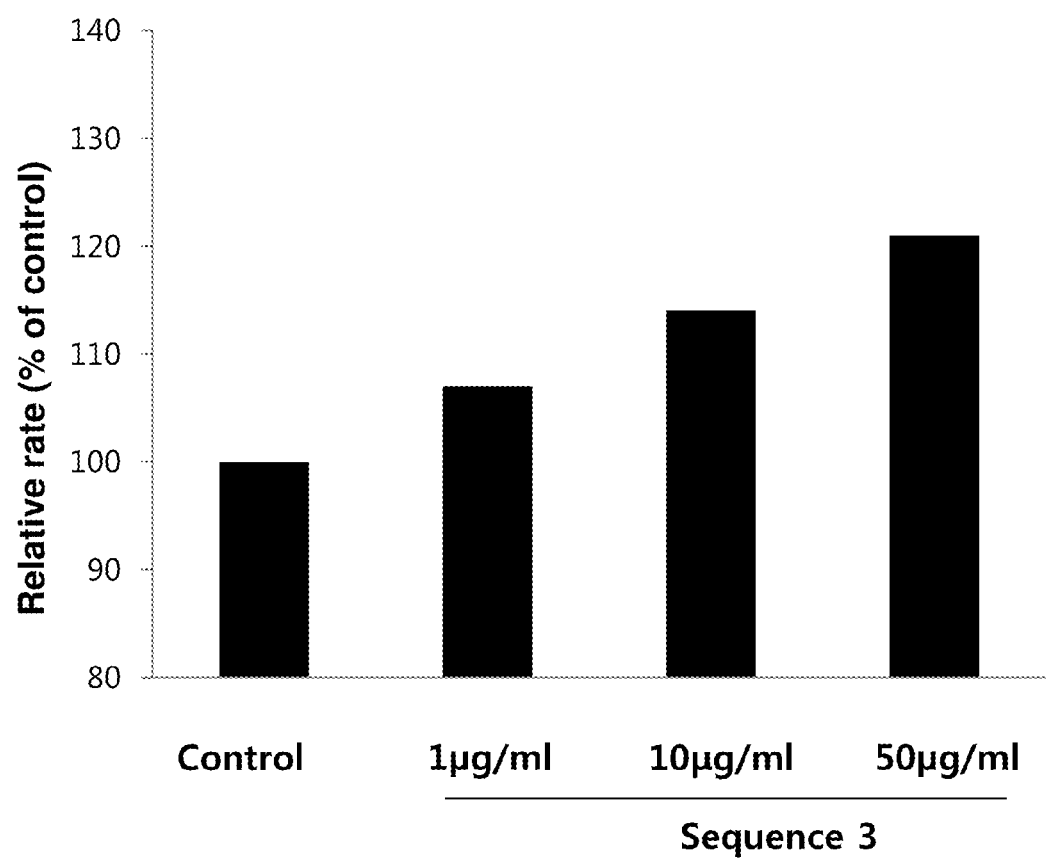
Figure 14A:
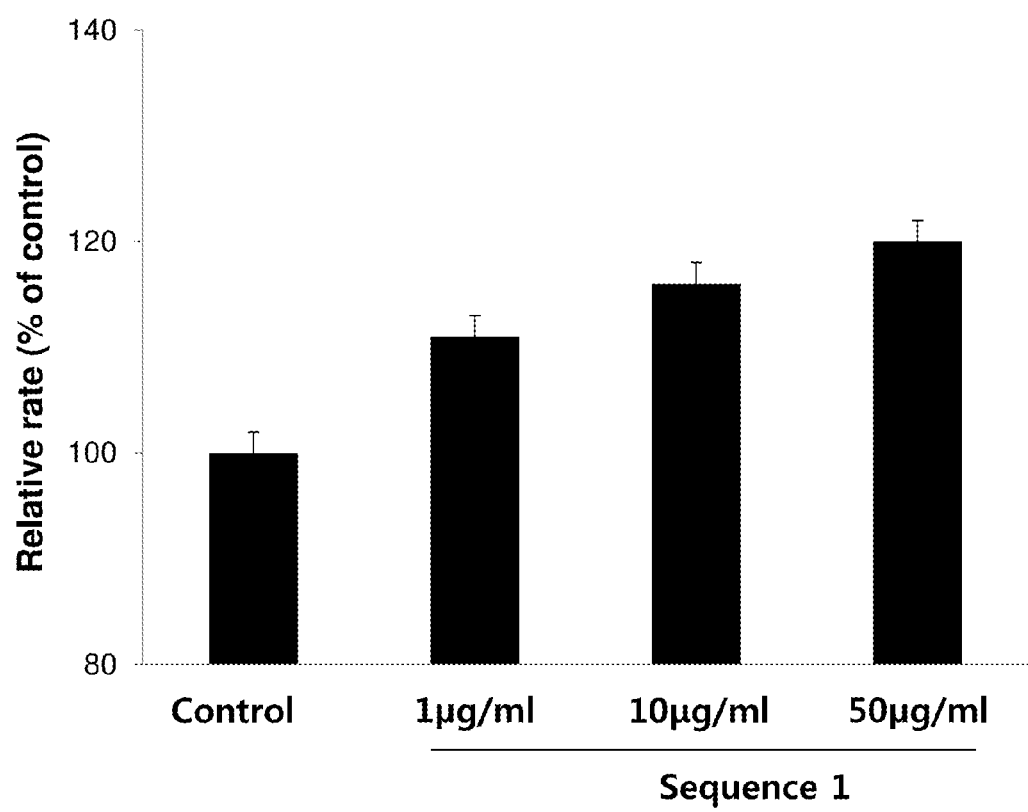
FIGS. 14a and 14b show results obtained by measuring the change in the proliferation of human hair follicle germinal matrix cells by the peptides of the present invention.
Figure 14B:
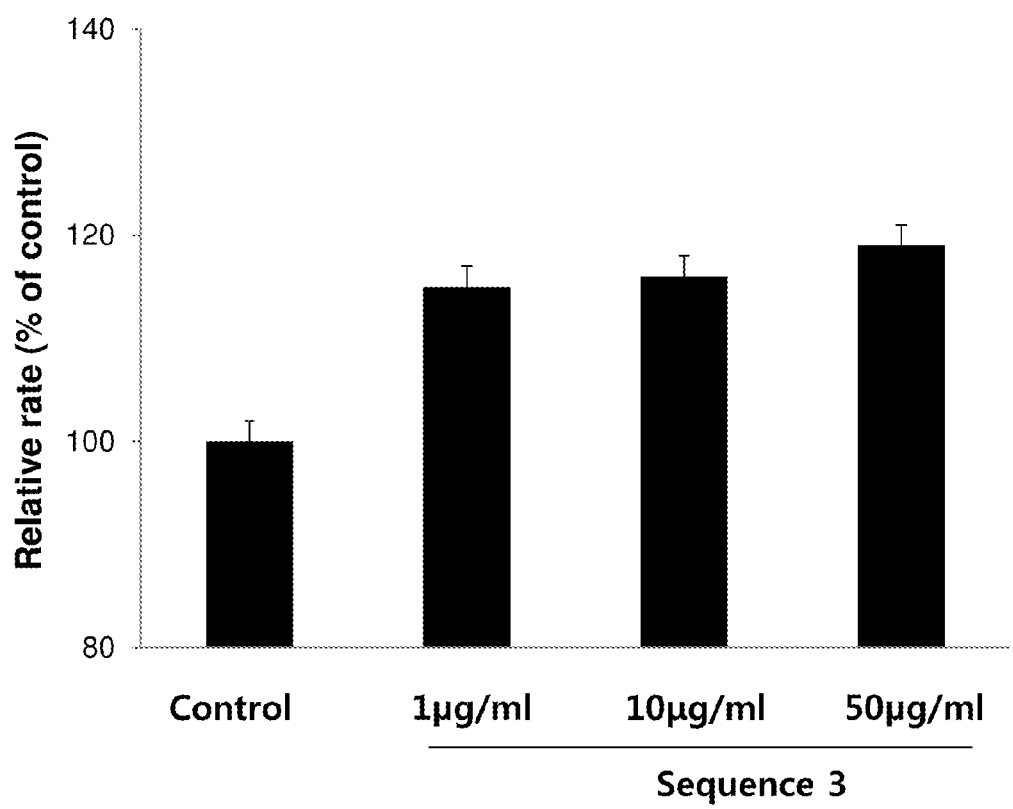
Figure 15A:
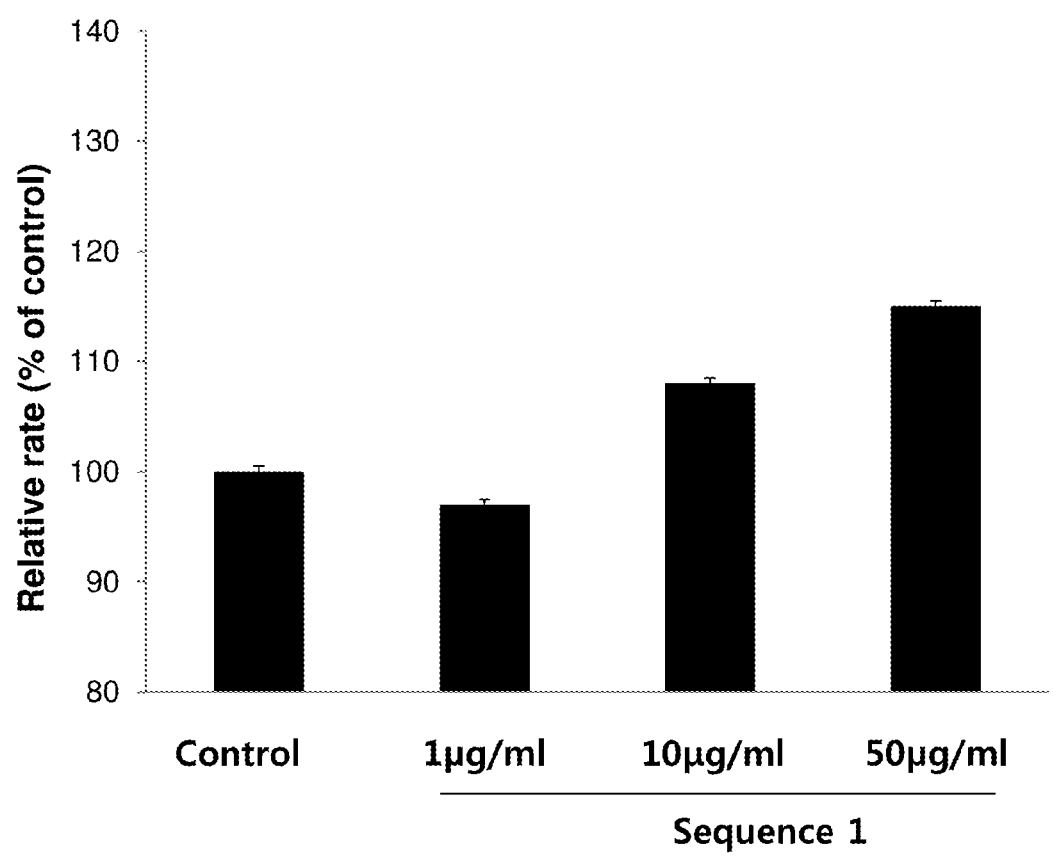
FIGS. 15a and 15b show results obtained by measuring the change in the proliferation of human umbilical vein endothelial cells by the peptides of the present invention.
Figure 15B:
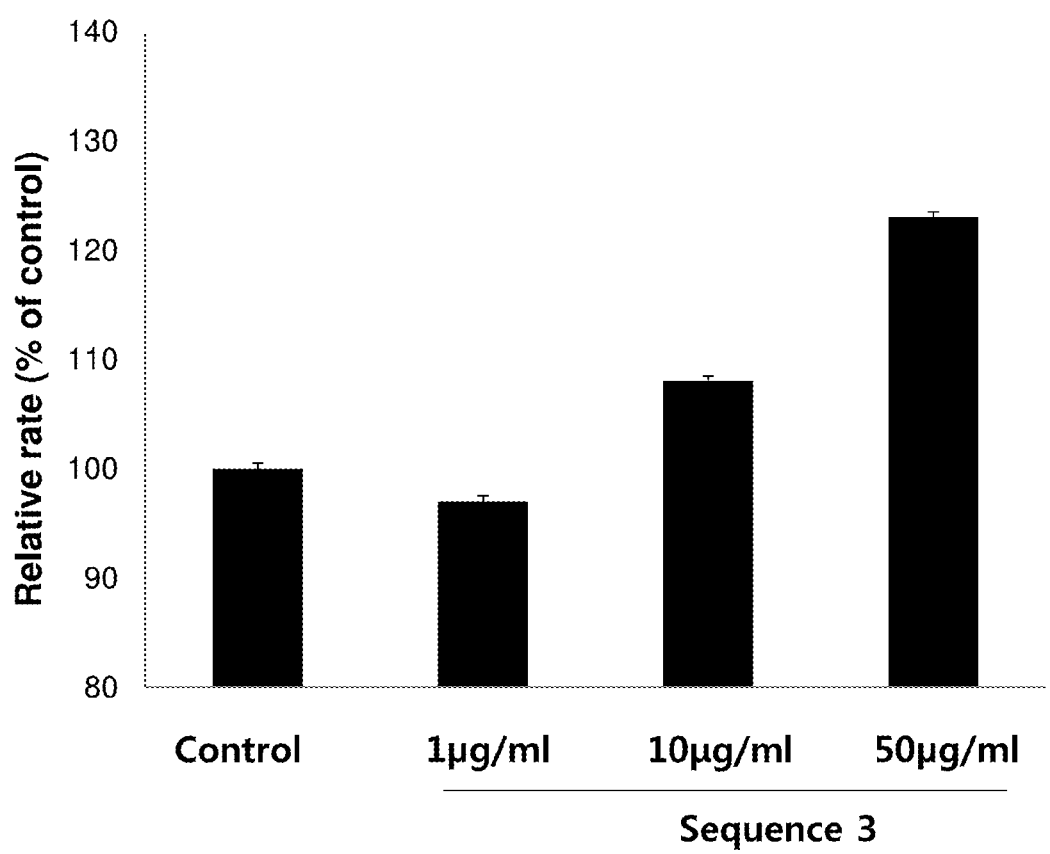

The mouse osteoblast line MC3T3-E1 cells were treated with the peptide of SEQ ID NO: 1, and then incubated for three days. As a result, it could be observed that the expression of osteogenic differentiation markers, osteoprotegerin (OPG), alkaline phosphatase (ALP), and bone sialoprotein (BSP) were increased in all of the positive control group, the group treated with 100 ng/ml BMP2, and the group treated with the peptide of SEQ ID NO: 1 (FIGS. 12a-12c).

Example 3: Evaluation of Hair Growth Ability 3-1. Observation of Cell Proliferation (Proliferation Assay)

In order to observe the cell proliferation effect on human hair follicle dermal papilla cells, human hair follicle germinal matrix cells, and human umbilical vein endothelial cells, which are main hair cells, each type of cells were seeded on a 96-well plate at a density of $3 \times 10^3$ cells/well, followed by incubation under conditions of 37° C. and 5% $CO_2$ for 24 hours. After the medium was exchanged with the same culture medium completely excluding serum, the cells were treated with the peptides at different concentrations (1 μg/ml, 10 μg/ml, and 50 μg/ml), followed by incubation under the same conditions for 72 hours. After the incubation supernatant was removed, the cells were immobilized using ethanol, and washed three times with phosphate buffer saline (PBS). The wash solution was removed, and the cells were stained through the treatment with colorimetric SRB solution. After the cells were sufficiently washed with 1% acetic acid, the cells were observed using a microscope to observe the state of living cells. The absorbance was read at UV light of 560 nm, thereby measuring the survival conditions of cells When the human hair follicle dermal papilla cells (HFDPC), human hair follicle germinal matrix cells (HFGMC), and human umbilical vein endothelial cells (HUVEC) were treated with the peptides of SEQ ID NO: 1 and SEQ ID NO: 3 at different concentrations and then incubated for 72 hours, the cell proliferation was increased in a concentration-dependent manner (FIGS. 13a-13b, FIGS. 14a-14b, and FIGS. 15a-15b).

3-2. Observation of Change in Cell Signaling Material

In order to observe the changes in the phosphorylation of ERK and the expression of PI3K, which are main signaling materials involved in cell proliferation in the human hair follicle dermal papilla cells, the cells were treated with the peptides of the present invention for 30 minutes and 60 minutes, and then subjected to western blotting using specific antibodies, thereby observing the pERK and PI3K changes. The test was carried out using anti-pERK antibody (Santa Cruz Biotechnology, USA) and anti-pPI3K antibody (Santa Cruz Biotechnology, USA).

The human hair follicle dermal papilla cells were seeded on a 6-well plate at a density of $1 \times 10^5$ cells/well, and then stabilized by incubation overnight, and then the cells were treated with the peptides at different concentrations (1 μg/ml and 10 μg/ml) by times (30 minutes and 60 minutes). The cells were treated with the cell lysis buffer to obtain a lysate, followed by protein quantification, and then western blotting was performed with respect to Phospho-ERK (pERK), PI3K, and β-catenin.

Figure 16:
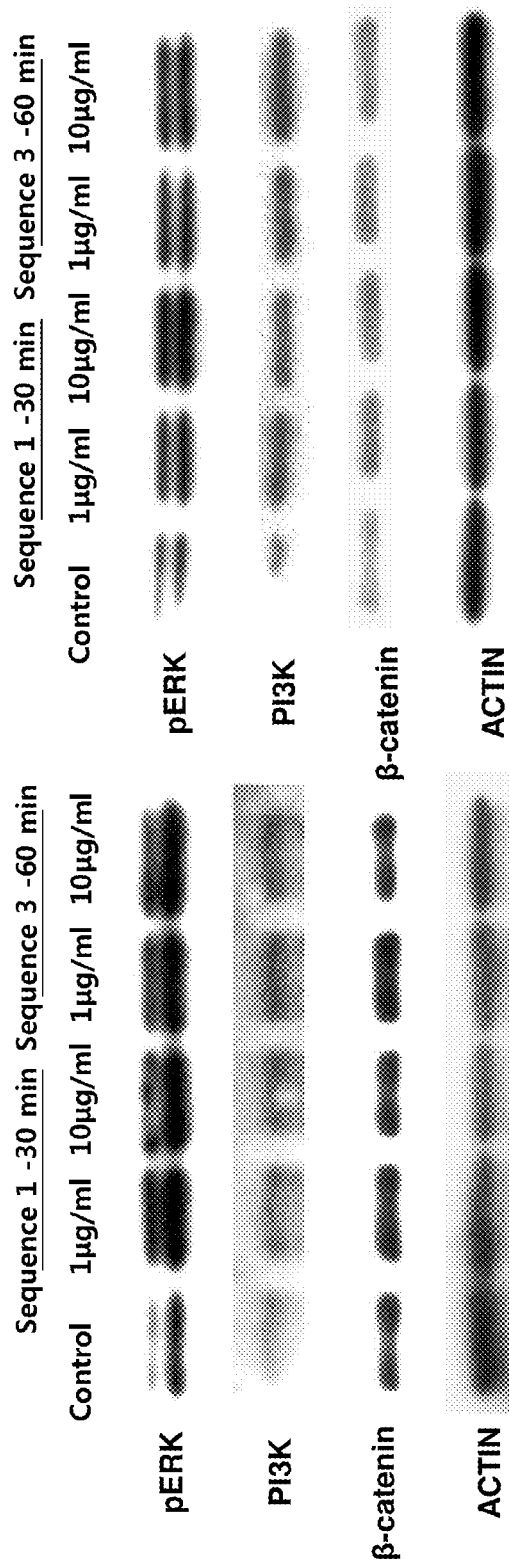
FIG. 16 shows results obtained by measuring the changes in ERK phosphorylation, PI3K expression, and β-catenin expression by the peptides of the present invention.

The human hair follicle dermal papilla cells were treated with the peptide of SEQ ID NO: 1 or SEQ ID NO: 3 for 30 minutes and 60 minutes, and then the changes in the cell proliferation-related signaling materials were observed. As a result, the phosphorylation of ERK and the level of PI3K, which are involved in cell proliferation, and the expression of β-catenin, which is involved in hair formation, were increased (FIG. 16).

3-3. Observation of Changes in Proteins Involved in Hair Growth

In order to observe the changes in the expression of IGF1, KGF, and Wnt3a, which are proteins involved in the development of hair roots in the human hair follicle dermal papilla cells, the cells were treated with the peptides of the present invention for 24 hours, and then subjected to western blotting using specific antibodies, thereby observing the changes in hair growth-related proteins.

The human hair follicle dermal papilla cells were seeded on a 6-well plate at a density of $1\times10^5$ cells/well. The cells were stabilized by the incubation overnight, and then treated with the peptides at different concentrations (0.1-50 μg/ml) for 24 hours. The cells were treated with the cell lysis buffer to obtain a lysate, followed by protein quantification, and then western blotting was performed with respect to IGF-1, KGF, and Wnt3a.

The test was carried out using anti-IGF-1 antibody (Santa Cruz Biotechnology, USA), anti-KGF antibody (Santa Cruz Biotechnology, USA), and anti-Wnt3a antibody (Santa Cruz Biotechnology, USA).

Figure 17:
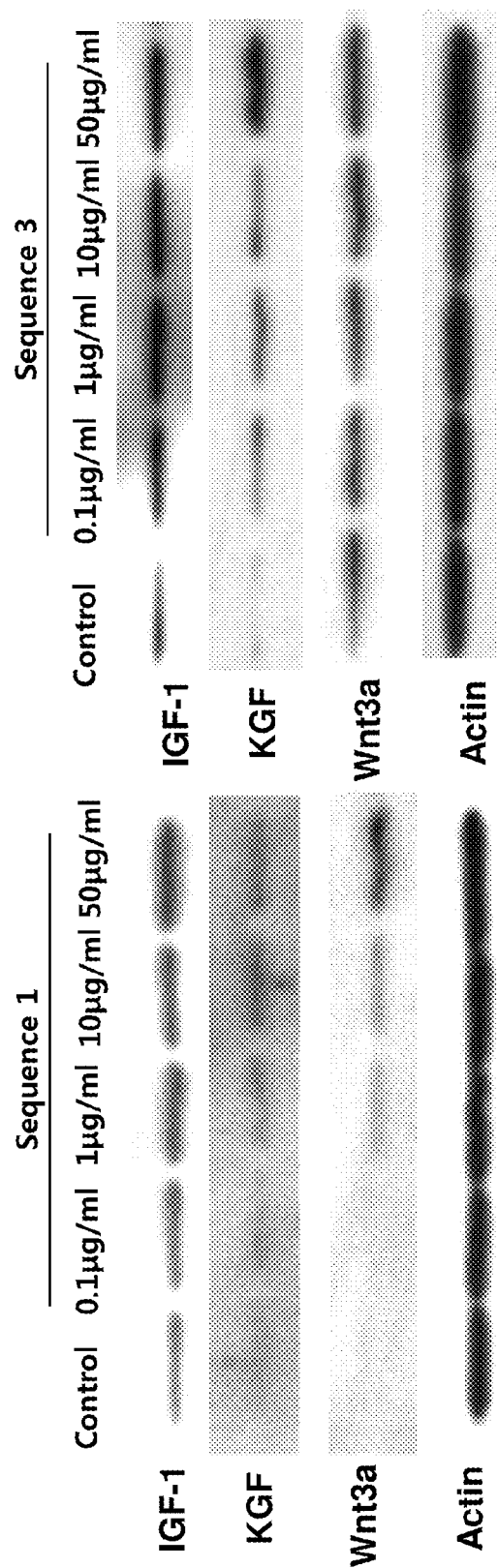
FIG. 17 shows results obtained by measuring the changes in the expression of IGF-1, KGF, and Wnt3a by the peptides of the present invention.

The human hair follicle dermal papilla cells were treated with the peptide of SEQ ID NO: 1 or SEQ ID NO: 3 at different concentrations for 24 hours. As a result, the expression of IGF-1, KGF, and Wnt3a, which are proteins involved in hair growth, was increased (FIG. 17).

3-4. Observation of Changes in Related Proteins by Hair Loss Causing Hormone

In order to observe the effects of the peptides on dihydrotestosterone (DHT), which is the hair loss causing hormone, the hair follicle dermal papilla cells were treated with 5 μg/ml DHT and the peptides of the present invention at different concentrations, and then the expression change of DKK-1, which is a hair loss-related protein, was observed. The cells were treated with DHT and the peptides for 48 hours, and then subjected to western blotting with respect to DKK-1 using specific antibodies, thereby observing the expression of DKK-1.

The human hair follicle dermal papilla cells were seeded on a 6-well plate at a density of $1\times10^5$ cells/well. The cells were stabilized by incubation overnight, and then treated with 5 μg/ml DHT (Sigma Aldrich) together with the peptides at different concentrations (1 μg/ml and 10 μg/ml) for 48 hours. The cells were treated with the cell lysis buffer to obtain a lysate, followed by protein quantification, and then western blotting was performed with respect to DKK-1 using anti-DKK-1 antibody (Santa Cruz Biotechnology, USA).

Figure 18:
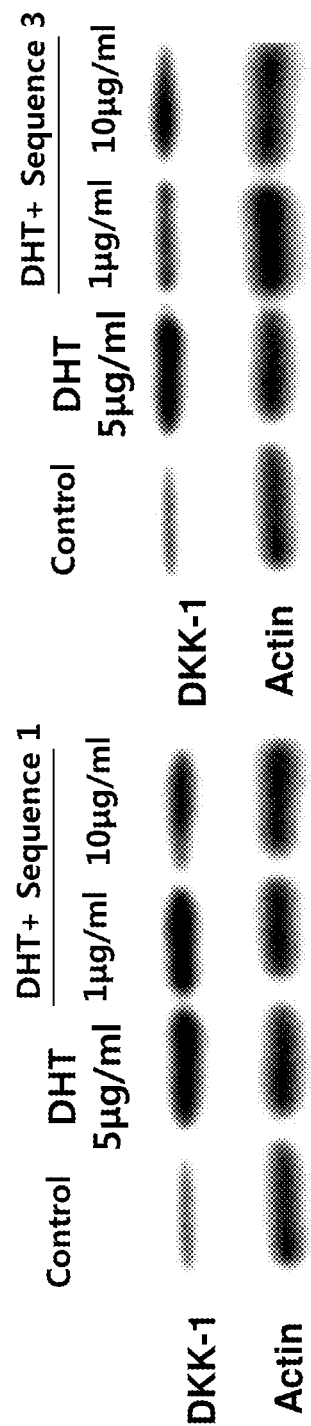
FIG. 18 shows results obtained by measuring the effects of the peptides of the present invention on the expression of DKK-1 increased by DHT treatment.

It was verified that the treatment of the human hair follicle dermal papilla cells with the hair loss causing hormone, DHT, increased the expression of DKK-1, which is the hair loss protein; and the expression of DKK-1 increased by DHT was reduced by the peptide of SEQ ID NO: 1 or SEQ ID NO: 3 (FIG. 18).

3-5. Observation of Change in Keratin Expression

In order to observe whether the peptide of SEQ ID NO: 1 or SEQ ID NO: 3 exhibits the hair growth promoting effect through the induction of keratinocyte differentiation promotion, the change in the expression of keratin, which is a cell differentiation marker material, was measured.

The keratinocyte line HaCaT cells were seeded on a 6-well plate at a density of $1\times10^5$ cells/well, and then incubated overnight. The cells were treated with the peptides at different concentrations (0.1 μg/ml, 1 μg/ml, and 10 μg/ml), and then incubated in an incubator at 37° C. for 24 hours. After the incubation-completed cells were collected, the cells were treated with RNA extraction solution (Easy Blue, Intron) to prepare RNA, and then cDNA was synthesized using RT pre-mix (Intron). RT-PCR was carried out using primers of respective markers (Ha3-II and keratin 14) and PCR pre-mix (Intron) to measure the changes in the expression of the markers.

Target-specific primer sequences used in PCR for keratinocyte differentiation markers were as follows: Ha3-II forward primer sequence, 5'-CAGAAGTATAGCAG-TAAGACAG-3' and Ha3-II reverse primer, 5'-CAAGAG-GAAAGTTTATTAGGC-3' (annealing temperature, 60° C.); Keratin14 forward primer sequence, 5'-GGACGCCCAC-CTTTCATCTTC-3' and Keratin14 reverse primer, 5'-ATCTGGCGGTTGGTGGAGG-3' (annealing temperature, 60° C.)

5 μl of PCR product was loaded on 1% agarose gel, followed by electrophoresis, and then the bands were investigated using Gel-Doc.

Figure 19:
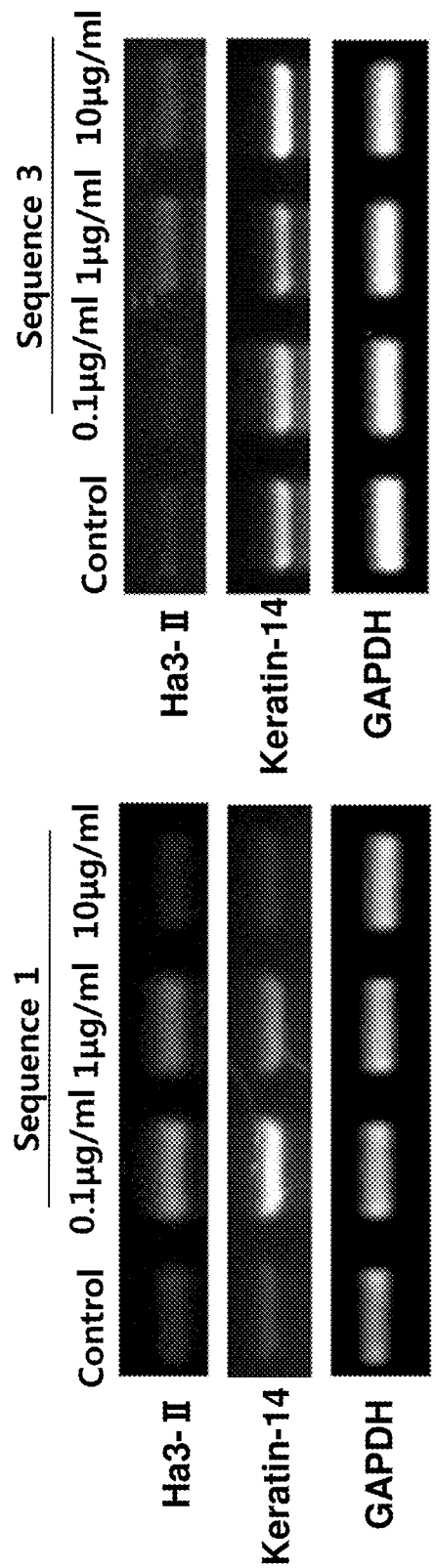
FIG. 19 shows results obtained by measuring the changes in the expression of Ha3-II and keratin-14 by the peptides of the present invention.

The keratinocytes were treated with the peptide of SEQ ID NO: 1 or SEQ ID NO: 3 at different concentrations, and then the mRNA expression levels of the differentiation markers, Ha3-II and keratin 14. As a result, it was verified that the two peptides exhibited the keratinocyte differentiation promoting effect (FIG. 19).

3-6. Observation of Mouse Whisker Growth Rate

The hair roots around whiskers of mice were isolated, and then treated with the peptides at a concentration of 50 μg/ml, followed by incubation under conditions of 37° C. and 5% $CO_2$ for eight days. On days 5 and 8, the effects of the peptides were investigated by observing the length of hairs.

Figure 20:
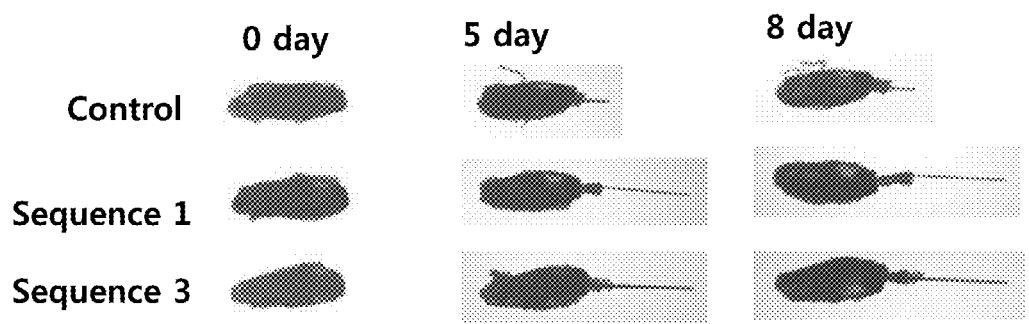
FIG. 20 shows results obtained by measuring the change in mouse whisker growth by the peptides of the present invention.

As a result of observing the hair growth change by the treatment with the peptides, the hair growth was observed to be faster in the treatment groups rather than the control group (FIG. 20).

Although the present invention has been described in detail with reference to the specific features, it will be apparent to those skilled in the art that this description is only for one embodiment and does not limit the scope of the present invention. Thus, the substantial scope of the present invention will be defined by the appended claims and equivalents thereof.

The invention claimed is:

1. A peptide having an anti-inflammatory activity, consisting of one amino acid sequence selected from the group consisting of the amino acid sequences of SEQ ID NO: 1, SEQ ID NO: 2, and SEQ ID NO: 3, optionally linked to an N- or C-terminal protecting group.

2. The peptide of claim 1, wherein the peptide inhibits the expression of an inflammatory cytokine.

3. The peptide of claim 1, wherein the peptide suppresses the proliferation of inflammatory cells.

4. A peptide having an osteogenic differentiation promoting activity, consisting of one amino acid sequence selected from the group consisting of the amino acid sequences of SEQ ID NO: 1, SEQ ID NO: 2, and SEQ ID NO: 3, optionally linked to an N- or C-terminal protecting group.

5. The peptide of claim 4, wherein the peptide increases the phosphorylation of PI3K, Smad1, Smad5, and SmadB.

6. The peptide of claim 4, wherein the peptide increases the expression of alkaline phosphatase (ALP), osteoprotegerin (OPG), and bone sialoprotein (BSP).

7. A peptide having a hair growth promoting activity, consisting of one amino acid sequence selected from the group consisting of the amino acid sequences of SEQ ID NO: 1 and SEQ ID NO: 3, optionally linked to an N- or C-terminal protecting group.

8. The peptide of claim 7, wherein the peptide promotes the proliferation of hair follicle cells or umbilical vein endothelial cells.

9. The peptide of claim 7, wherein the peptide increases the phosphorylation of ERK.

10. The peptide of claim 7, wherein the peptide increases the expression of PI3K, β-catenin, KGF, and Wnt3a.

11. The peptide of claim 7, wherein the peptide reduces the expression of DKK-1.

12. A method for treating a bone disease in a subject, the method comprising administering, to the subject, a composition comprising, as an active ingredient, the peptide of claim 4, wherein the bone disease is selected from the group consisting of osteoporosis, osteogenesis imperfecta, osteomalacia, bone necrosis, rickets, osteomyelitis, alveolar bone loss Paget's disease of bone, hypercalcemia, primary hyperparathyroidism, metastatic bone diseases, myeloma, bone loss in rheumatoid arthritis, bone loss resulting from cancers, fibrous dysplasia, aplastic bone diseases, metabolic bone diseases and bone mass loss with age.

13. A method for preventing hair loss or promoting hair growth, the method comprising locally administering, to a subject, a composition comprising, as an active ingredient, the peptide of claim 7.

14. The peptide of claim 1, wherein the peptide is linked to an N- or C-terminal protecting group.

15. The peptide of claim 14, wherein the N- or C-terminal protecting group is selected from the group consisting of an acetyl group, a fluorenyl methoxy carbonyl group, a formyl group, a palmitoyl group, a myristyl group, a stearyl group, and polyethylene glycol (PEG).

16. The peptide of claim 4, wherein the peptide is linked to an N- or C-terminal protecting group.

17. The peptide of claim 16, wherein the N- or C-terminal protecting group is selected from the group consisting of an acetyl group, a fluorenyl methoxy carbonyl group, a formyl group, a palmitoyl group, a myristyl group, a stearyl group, and polyethylene glycol (PEG).

18. The peptide of claim 7, wherein the peptide is linked to an N- or C-terminal protecting group.

19. The peptide of claim 18, wherein the N- or C-terminal protecting group is selected from the group consisting of an acetyl group, a fluorenyl methoxy carbonyl group, a formyl group, a palmitoyl group, a myristyl group, a stearyl group, and polyethylene glycol (PEG).

20. The peptide of claim 1, which consists of the amino acid sequence selected from the group consisting of the amino acid sequences of SEQ ID NO: 1, SEQ 1p NO: 2, and SEQ ID NO: 3.

21. The peptide of claim 4, which consists of the amino acid sequence selected from the group consisting of the amino acid sequences of SEQ ID NO: 1, SEQ ID NO: 2, and SEQ ID NO: 3.

* * * * *

SEQUENCE LISTING

<160> NUMBER OF SEQ ID NOS: 13

<210> SEQ ID NO 1
<211> LENGTH: 10
<212> TYPE: PRT
<213> ORGANISM: Artificial Sequence
<220> FEATURE:
<223> OTHER INFORMATION: Synthetic construct

<400> SEQUENCE: 1

Ala Cys Arg Ser Ala Ile Gly Arg Pro Cys
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic construct

<400> SEQUENCE: 2

Ala Cys Phe Thr Arg Thr Ser His Ala Cys
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic construct

<400> SEQUENCE: 3

Ala Cys Asp Gly Arg Thr Gln Ala Leu Cys
1               5                   10

<210> SEQ ID NO 4
<211> LENGTH: 20
<212> TYPE: DNA
<213> ORGANISM: Artificial Sequence
<220> FEATURE:
<223> OTHER INFORMATION: Synthetic construct

<400> SEQUENCE: 4
ctgcctggga agaagatcag                                          20

<210> SEQ ID NO 5
<211> LENGTH: 20
<212> TYPE: DNA
<213> ORGANISM: Artificial Sequence
<220> FEATURE:
<223> OTHER INFORMATION: Synthetic construct

<400> SEQUENCE: 5
ttgtgaagct gtgcaggaac                                          20

<210> SEQ ID NO 6
<211> LENGTH: 20
<212> TYPE: DNA
<213> ORGANISM: Artificial Sequence
<220> FEATURE:
<223> OTHER INFORMATION: Synthetic construct

<400> SEQUENCE: 6
ccagcaggtt tctctcttgg                                          20

<210> SEQ ID NO 7
<211> LENGTH: 20
<212> TYPE: DNA
<213> ORGANISM: Artificial Sequence
<220> FEATURE:
<223> OTHER INFORMATION: Synthetic construct

<400> SEQUENCE: 7
ctgggagrcr catcctgagc                                          20

```
<210> SEQ ID NO 8
<211> LENGTH: 20
<212> TYPE: DNA
<213> ORGANISM: Artificial Sequence
<220> FEATURE:
<223> OTHER INFORMATION: Synthetic construct

<400> SEQUENCE: 8
aaagtgaagg aaagcgacga                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic construct

<400> SEQUENCE: 9
gttccttctg cacctgcttc                                               20

<210> SEQ ID NO 10
<211> LENGTH: 22
<212> TYPE: DNA
<213> ORGANISM: Artificial Sequence
<220> FEATURE:
<223> OTHER INFORMATION: Synthetic construct

<400> SEQUENCE: 10
cagaagtata gcagtaagac ag                                            22

<210> SEQ ID NO 11
<211> LENGTH: 21
<212> TYPE: DNA
<213> ORGANISM: Artificial Sequence
<220> FEATURE:
<223> OTHER INFORMATION: Synthetic construct

<400> SEQUENCE: 11
caagaggaaa gtttattagg c                                             21

<210> SEQ ID NO 12
<211> LENGTH: 21
<212> TYPE: DNA
<213> ORGANISM: Artificial Sequence
<220> FEATURE:
<223> OTHER INFORMATION: Synthetic construct

<400> SEQUENCE: 12
ggacgcccac ctttcatctt c                                             21

<210> SEQ ID NO 13
<211> LENGTH: 19
<212> TYPE: DNA
<213> ORGANISM: Artificial Sequence
<220> FEATURE:
<223> OTHER INFORMATION: Synthetic construct

<400> SEQUENCE: 13
atctggcggt tggtggagg                                                19
```